United States Patent
Phifer et al.

(10) Patent No.: US 11,975,084 B2
(45) Date of Patent: May 7, 2024

(54) COMPOSITION FOR APPLICATION TO A SURFACE OF SKIN OF A USER

(71) Applicant: Kao USA Inc., Cincinnati, OH (US)

(72) Inventors: Kevin Phifer, Cincinnati, OH (US); Lei Zhao, Mason, OH (US); Mathieu Gervais, West Chester, OH (US); Wael Boutros, Mason, OH (US)

(73) Assignee: Kao USA Inc., Cincinnati, OH (US)

( * ) Notice: Subject to any disclaimer, the term of this patent is extended or adjusted under 35 U.S.C. 154(b) by 192 days.

(21) Appl. No.: 17/674,046

(22) Filed: Feb. 17, 2022

(65) Prior Publication Data

US 2023/0255862 A1     Aug. 17, 2023

(51) Int. Cl.
| | | |
|---|---|---|
| *A61K 8/34* | (2006.01) | |
| *A61K 8/06* | (2006.01) | |
| *A61K 8/58* | (2006.01) | |
| *A61K 8/60* | (2006.01) | |
| *A61Q 17/00* | (2006.01) | |
| *A61Q 19/00* | (2006.01) | |

(52) U.S. Cl.
CPC ............. *A61K 8/345* (2013.01); *A61K 8/062* (2013.01); *A61K 8/585* (2013.01); *A61K 8/60* (2013.01); *A61Q 17/005* (2013.01); *A61Q 19/007* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 8,980,344 B2 | 3/2015 | Gross | |
| 2012/0121721 A1 | 5/2012 | James | |
| 2014/0178444 A1 | 6/2014 | Stadler et al. | |
| 2016/0206543 A1* | 7/2016 | Tittl ..................... | A61K 9/06 |
| 2021/0093529 A1* | 4/2021 | LaRosa ................ | A61K 8/445 |

OTHER PUBLICATIONS

Covergirl® Clean Fresh Skincare Weightless Water Cream; https://www.covergirl.com/en_us/skincare/cf-skincare-weightless-water-cream.html. Accessed Feb. 18, 2022.
Ulta® Beauty, Covergirl® Clean Fresh Weightless Water Cream Moisturizer; https://www.ulta.com/p/clean-fresh-weightless-water-cream-moisturizer-pimprod2029920. Accessed on Feb. 18, 2022.
Dermstore Perricone MD Hyaluronic Intensive Moisturizer; https://www.dermstore.com/perricone-md-hpe-hyaluronic-intenvsive-moisturizer/11833559.html; Accessed on Jun. 21, 2022.
INCIDecoder Perricone MD H2 Elemental Energy Hydrating Cloud Cream; https://incidecoder.com/products/perricone-md-h2-elemental-energy-hydrating-cloud-cream; Accessed on Jun. 21, 2022.
Perricone MD High Potency Hyaluronic Intensive Hydrating Serum; https://www.perriconemd.com/high-potency-hyaluronic-intensive-hydrating-serum/13156918.html; Accessed on Jun. 21, 2022.
SkinSAFE Perricone MD H2 Elemental Energy Hydrating Cloud Cream; https://www.skinsafeproducts.com/perricone-md-h2-elemental-energy-hydrating-cloud-cream-1-7-fl-0z#ingredients; Accessed on Jun. 21, 2022.
Internal Applicant document showing the dates of commercialization for the subject skin moisturizing composition.
Peter Thomas Roth "Water Drench" Cloud Cream; Amazon.com, accessed on Jan. 26, 2022.
Tables 5-8 of the subject application disclose the ingredient listing of the multiple comparative samples (CS1-CS11) mentioned in the background section of this disclosure.
Internal Applicant document showing the dates of commercialization for the subject skin moisturizing composition, specifically Inventive Example 3 (IE3).
Premium Beauty News: Natural cosmetic preservation with Spectrastat complete solutions; https://www.premiumbeautynews.com/en/natural-cosmetic-preservation-with,16466, accessed on Feb. 24, 2022.
Lumene Glow Boost Essence; https://www.lumene.com/us/skincare/collection/nordic-c-valo/nordiccvalo/glow-boost-essence--80225.html; Accessed on Jul. 20, 2022.

\* cited by examiner

*Primary Examiner* — Nannette Holloman
(74) *Attorney, Agent, or Firm* — Frost Brown Todd LLP

(57) ABSTRACT

A composition for application to a surface of skin includes from 0.1% to 1% by weight of at least one antimicrobial agent for disrupting a microbial cell, from 0.025% to 0.2% by weight of sodium gluconate as a micro-preservative potentiator also for disrupting a microbial cell, from 0.5% to 8% by weight of ethylhexyl isononanoate as an emollient for moisturizing a surface of skin, and from 0.005% to 0.04% by weight of a hyaluronic complex for hydrating the surface of skin. The hyaluronic complex includes a combination of hyaluronic acid, a salt derivative of hyaluronic acid, phenoxyethanol and water.

13 Claims, 12 Drawing Sheets

COMPOSITION FOR APPLICATION TO A SURFACE OF SKIN OF A USER

FIELD OF THE INVENTION

The present invention relates to a composition, and in particular, a composition for application to a surface of skin of a user.

BACKGROUND OF THE INVENTION

According to an online survey conducted by Kao USA, Inc. in March of 2019, women aged 20-44 years old who have normal, dry, and oily skin types require a skin care product (e.g., a body cream or a lotion) that provides very light to moderate moisture to the skin. Many of these women are of Caucasian or African descent and use a skin care product more than once a day. For this demographic, desired characteristics of a skin care product include noticeable breathability, a light feel, and a refreshed feel. (For the purpose of this application, the term "breathability" is defined as the flow of water vapor from within and under a surface of skin to an external environment.) Desired performance features of a skin care product include easy application to skin, quick absorption, a soft and smooth feel, reduced stickiness, reduced greasiness, a noticeable shine, a clean and fresh scent, and a natural feel (i.e., not an obvious feeling of a skin care product having been applied). Concerns of this demographic about skin care products include a heavy/messy/sticky feel upon application, slow absorption, and inclusion of ingredients that are known, or perceived, to be unsafe/unclean.

Body creams and lotions are meant to moisturize, hydrate, and relieve dryness of skin on a user. However, many such products may contain ingredients that create a feeling of greasiness, stickiness, and heaviness to the skin (for instance, petrolatum). Additionally, many such products may be slow to absorb into the skin and may contain ingredients about which consumers have negative perceptions, for example, parabens and butylated hydroxytoluene (BHT).

There are many ingredients that are commonly used in formulations for body creams and lotions. Examples of current formulations that contain common ingredients include Nivea® Breathable Nourishing Body Lotion, Nivea® Essentially Enriched, Neutrogena® Hydro Boost Body Gel Cream, Neutrogena® Hydro Boost Hand Gel Cream, Neutrogena® Hydro Boost Whipped Body Balm, petrolatum (e.g., Regent White Pet USP by Calumet Specialty Products Partners, L.P.), Eucerin® Original Healing, Vaseline® Petroleum Jelly, and Water Drench® by Peter Thomas Roth. Other such formulations can also be found in U.S. Pat. No. 8,980,344, US 20140178444, US20120121721, and US20210093529.

Current commercialized products by Applicant include Jergens® Ultra Healing, Jergens® Soothing Aloe Moisturizer, and Jergens® Shea Butter Moisturizer.

Thus, a need exists for a composition for use as a body cream/lotion that provides both the benefits provided by current products, as well as reduced greasiness, stickiness, and heaviness when applied to skin, while also excluding certain ingredients.

SUMMARY OF THE INVENTION

The present invention provides a composition that includes from 0.1% to 1%, by weight, of at least one antimicrobial agent for disrupting a microbial cell, from 0.025% to 0.2%, by weight, of sodium gluconate as a micro-preservative potentiator also for disrupting a microbial cell, from 0.5% to 8%, by weight, of ethylhexyl isononanoate as an emollient for moisturizing a surface of skin, and from 0.005% to 0.04%, by weight, of a hyaluronic complex for hydrating the surface of skin. The hyaluronic complex includes a combination of sodium hyaluronate, hyaluronic acid, phenoxyethanol, and water.

The composition of the present invention aims to provide breathability and a comfortable, non-greasy feel to a user upon application to hand and body, while avoiding certain ingredients undesired by consumers. The present composition was found to be competitive with current commercial products with respect to aspects such as friction against skin, external hydration of skin, and breathability of skin. Bound by no particular theory, it is believed that a combination of at least one antimicrobial agent, sodium gluconate, ethylhexyl isononanoate, and a hyaluronic complex contributes to these features.

DETAILED DESCRIPTION OF THE INVENTION

Solvent

Figure 1:
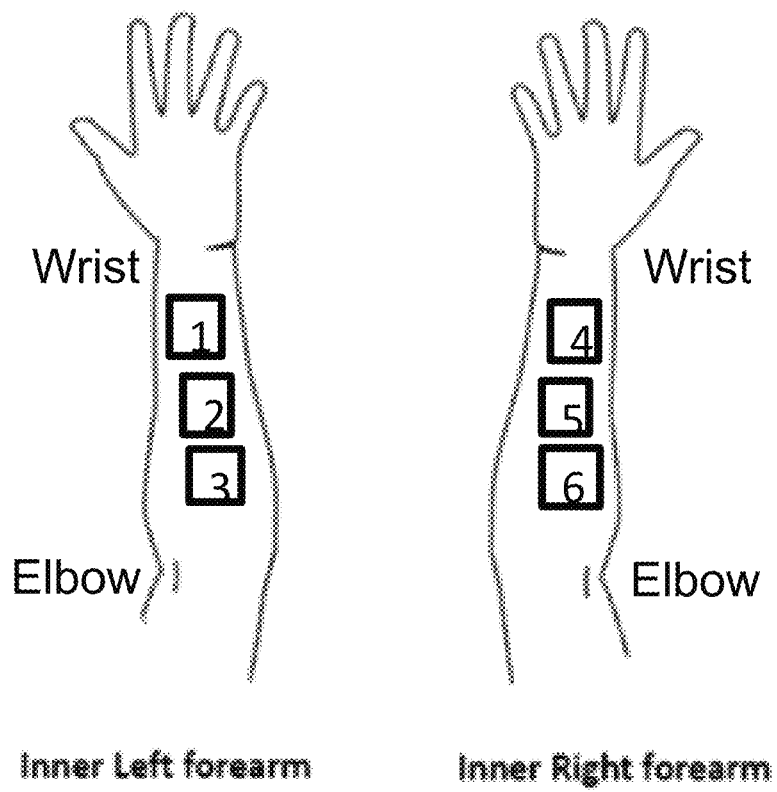
FIG. 1 illustrates a diagram of a pair of human forearms marked with test sites.

A composition, for application to a surface of skin of a user, includes a solvent. In one instance, the solvent is water. In such an instance, the water is present in an amount necessary to total a weight of the composition to 100%, after inclusion of all other ingredients. The amount of water typically ranges from 75% to 85% by weight of the composition. The water serves as a medium for external phase oil-in-water emulsions and as a solvent for water-soluble materials. In a particular instance, the water is deionized water.

Humectants

The composition includes at least one humectant for hydrating the surface of skin. Such humectants include the following:

Glycerin (vegetable grade) may be included to hydrate and create a soft feeling on the surface of skin. Glycerin may be present in an amount ranging from 1.5% to 16%, or from 3% to 12%, or from 4.5% to 10% by weight of the composition. The amount can also range from 1.5%, or 3%, or 4.5% to 10%, or 12%, or 16% by weight of the composition. In one instance, the composition includes 6% glycerin by weight. In another instance, the composition includes 8% glycerin by weight.

The composition may also include a blend of water, xylitylglucoside, anhydroxylitol, and xylitol as a supplemental humectant to glycerin, also hydrating and creating a soft feeling on the surface of skin. Such a blend may be present in an amount ranging from 0.25% to 2%, or from 0.5% to 1.5%, or from 0.75% to 1.25% by weight of the composition. The amount can also range from 0.25%, or 0.5%, or 0.75% to 1.25%, or 1.5%, or 2% by weight of the composition. In one instance, the composition includes 1 of such a blend by weight.

Butylene glycol may be included to further hydrate and creates a soft feeling on the surface of skin, and additionally reduce stickiness of the composition in relation to the surface of skin. Butylene glycol may be present in an amount ranging from 0.75% to 6%, or from 1.5% to 4.5%, or from 2.25% to 3.75% by weight of the composition. The amount can also range from 0.75%, or 1.5%, or 2.25% to 3.75%, or 4.5%, or 6% by weight of the composition. In one instance, the composition includes 3% butylene glycol by weight.

The composition may include combinations of the above humectants.

Thickeners

The composition includes at least one thickener for providing emulsion stability to the composition. Such thickeners may include the following:

Xanthan gum may be included to stabilize emulsion formation of the composition and allow for spreading and slipping of the composition on the surface of skin. Xanthan gum may be present in an amount ranging from 0.05% to 0.4%, or from 0.1% to 0.3%, or from 0.15% to 0.25% by weight of the composition. The amount can also range from 0.05%, or 0.1%, or 0.15% to 0.25%, or 0.3%, or 0.4% by weight of the composition. In one instance, the composition includes 0.2% xanthan gum by weight.

A blend of acrylates and $C_{10-30}$ alkyl acrylate crosspolymer may be included to stabilize emulsion formation of, and thicken, the composition. The blend also allows for spreading of the composition on the surface of skin. Such a blend may be present in an amount ranging from 0.025% to 0.2%, or from 0.05% to 0.15%, or from 0.075% to 0.13% by weight of the composition. The amount can also range from 0.025%, or 0.05%, or 0.075% to 0.13%, or 0.15%, or 0.2% by weight of the composition. In one instance, the composition includes 0.1% of such a blend by weight.

A blend of water, sodium acrylate, sodium acryloyldimethyl taurate copolymer (a thickening agent for thickening the composition), $C_{15-19}$ alkane oil (an emollient oil and carrier for dispersing the thickening agent within the composition), polyglyceryl-6 laurate (a non-ionic emulsifier and stabilizer for aiding the emollient oil in dispersing the thickening agent once added to water, the solvent of the composition), and polyglycerin-6 may be included to stabilize emulsion formation of, and thicken, the composition. The blend also allows for spreading of the composition on the surface of skin. Sodium acryloyldimethyl taurate copolymer is suspended in $C_{15-19}$ alkane oil and is present with polyglyceryl-6 laurate and polyglycerin-6 for dispersion within the composition when added to water (i.e., the solvent of the composition). Other non-ionic emulsifiers may be present as well. Such a blend may be included in an amount ranging from 0.6% to 5%, or from 1.25% to 3.75%, or from 1.85% to 3.15% by weight of the composition. The amount can also range from 0.6%, or 1.25%, or 1.85% to 3.15%, or 3.75%, or 5% by weight of the composition. In one instance, the composition includes 2.5% of such a blend by weight.

A blend of water, polyacrylamide (another thickening agent for thickening the composition), $C_{13-14}$ isoparaffin oil (another emollient oil and carrier for dispersing the thickening polymer within the composition), and laureth-7 (another non-ionic emulsifier and stabilizer for aiding emollient oil in dispersing the thickening polymer once added to water, the solvent of the composition) may be included to stabilize emulsion formation of, and thicken, the composition. The blend also allows for spreading of the composition on the surface of skin. Polyacrylamide is suspended in $C_{13-14}$ isoparaffin oil and is present with laureth-7 for dispersion when added to water (i.e., the solvent of the composition). Other non-ionic emulsifiers may be present as well. Such a blend may be included in an amount ranging from 0.35% to 3%, or from 0.75% to 2.25%, or from 1% to 2% by weight of the composition. The amount can also range from 0.35%, or 0.75%, or 1% to 2%, or 2.25%, or 3% by weight of the composition. In one instance, the composition includes 1.5% of such a blend by weight.

Sodium acrylates crosspolymer-2 may be included to stabilize emulsion formation of, and thicken, the composition, and give the composition a whipped feel when applied to the surface of skin. Sodium acrylates crosspolymer-2 may be included in an amount ranging from 0.2% to 1.6%, or from 0.4% to 1.2%, or from 0.6% to 1% by weight of the composition. The amount can also range from 0.2%, or 0.4%, or 0.6% to 1%, or 1.2%, or 1.6% by weight of the composition. In one instance, the composition includes 0.8% sodium acrylates crosspolymer-2 by weight.

The composition may include combinations of the above thickeners.

Emollients

The composition includes at least one emollient for moisturizing the surface of skin. Such emollients may include the following:

A blend of caprylic triglyceride and capric triglyceride may be included to hydrate and create a soft feeling on the surface of skin. Such a blend may be included in an amount ranging from 0.25% to 2%, or from 0.5% to 1.5%, or from 0.75% to 1.25% by weight of the composition. The amount can also range from 0.25%, or 0.5%, or 0.75% to 1.25%, or 1.5%, or 2% by weight of the composition. In one instance, the composition includes 1% of such a blend.

Dicaprylyl ether may be included to hydrate and create a soft, dry feeling on the surface of skin. Dicaprylyl ether may be included in an amount ranging from 0.1% to 1%, or from 0.25% to 0.75%, or from 0.35% to 0.65% by weight of the composition. The amount can also range from 0.1%, or 0.25%, or 0.35% to 0.65%, or 0.75%, or 1% by weight of the composition. In one instance, the composition includes 0.5% dicaprylyl ether by weight.

Cetyl esters wax NF (National Formulary) may be included, also for hydrating and creating a soft, dry feeling on the surface of skin, and furthermore providing structure to emulsion formation of the composition. Cetyl esters wax may be included in an amount ranging from 0.06% to 0.5%, or from 0.1% to 0.4%, or from 0.15% to 0.35% by weight of the composition. The amount can also range from 0.06%, or 0.1%, or 0.15% to 0.35%, or 0.4%, or 0.5% by weight of the composition. In one instance, the composition includes 0.25% cetyl esters wax by weight.

Isopropyl palmitate may be included, also for creating a soft feeling on the surface of skin. Isopropyl palmitate may be included in an amount ranging from 0.25% to 2%, or from 0.5% to 1.5%, or from 0.75% to 1.25% by weight of the composition. The amount can also range from 0.25%, or 0.5%, or 0.75% to 1.25%, or 1.5%, or 2% by weight of the composition. In one instance, the composition includes 1% isopropyl palmitate by weight.

Glyceryl dilaurate may be included, also for hydrating and creating a soft feeling on the surface of skin, and furthermore stabilizing emulsion formation of the composition. Glyceryl dilaurate may be included in an amount ranging from 0.25% to 2%, or from 0.5% to 1.5%, or from 0.75% to 1.25% by weight of the composition. The amount can also range from 0.25%, or 0.5%, or 0.75% to 1.25%, or 1.5%, or 2% by weight of the composition. In one instance, the composition includes 1% A glyceryl dilaurate by weight.

Shea butter (butyrospermum parkii butter) may be included, also for hydrating and creating a soft feeling on the surface of skin, and furthermore allowing for a shine of the composition when applied to the surface of skin. Shea butter may be included in an amount ranging from 0.5% to 4%, or from 1% to 3%, or from 1.5% to 2.5% by weight of the composition. The amount can also range from 0.5%, or 1%, or 1.5% to 2.5%, or 3%, or 4% by weight of the composition. In one instance, the composition includes 2% shea butter by weight.

The composition may include combinations of the above emollients.

Non-ionic Primary Emulsifiers

The composition includes at least one non-ionic primary emulsifier for providing hydrophilic-lipophilic balance (HLB) to the composition. Such non-ionic primary emulsifiers include a combination of the following: glyceryl stearate (alone), ceteareth-20, and a blend of glyceryl stearate and PEG-100 stearate.

In one instance, the blend of glyceryl stearate and PEG-100 stearate may be present in an amount ranging from 0.0075% to 2%, or from 0.015% to 1.4%, or from 0.02% to 1.15% by weight of the composition. The amount can also range from 0.0075%, or 0.015%, or 0.02% to 1.15%, or 1.4%, or 2% by weight of the composition. In another instance, such a blend is present at an amount of 0.9% by weight of the composition. In a further instance, such a blend is present at an amount of 0.03% by weight of the composition.

In one instance, glyceryl stearate is present in an amount ranging from 0.0075% to 0.06%, or from 0.015% to 0.045%, or from 0.02% to 0.04% by weight of the composition. The amount can also range from 0.0075%, or 0.015%, or 0.02% to 0.04%, or 0.045%, or 0.06% by weight of the composition. In another instance, glyceryl stearate is present at an amount of 0.03% by weight of the composition.

In one instance, ceteareth-20 is present in amount ranging from 0.06% to 0.5%, or from 0.1% to 0.4%, or from 0.15% to 0.35% by weight of the composition. The amount can also range from 0.06%, or 0.1%, or 0.15% to 0.35%, or 0.4%, or 0.5% by weight of the composition. In another instance, ceteareth-20 is present at an amount of 0.25% by weight of the composition.

The composition may include combinations of the above non-ionic primary emulsifiers.

Secondary Emulsifier

The composition includes a secondary emulsifier for stabilizing emulsion formation of the composition. In one instance, the secondary emulsifier is stearic acid (vegetable grade). Stearic acid stabilizes emulsion formation of the composition by forming sodium stearate. Sodium stearate is formed by combining an amount of from 0.05% to 6% by mass of stearic acid (a linear saturated fatty acid having 12 to 22 carbon atoms) with an amount of from 0.01% to 1% by mass of sodium hydroxide (an inorganic base). That is, stearic acid reacts with sodium hydroxide (detailed later) in the composition to form sodium stearate. Stearic acid is present in an amount ranging from 0.06% to 0.5%, or from 0.1% to 0.4%, or from 0.15% to 0.35% by weight of the composition. The amount can also range from 0.06%, or 0.1%, or 0.15% to 0.35%, or 0.4%, or 0.5% by weight of the composition. In one instance, the composition includes 0.25% stearic acid by weight.

Silicones

The composition includes at least one silicone for providing lubrication to the surface of skin. Such silicones may include the following:

Dimethicone reduces stickiness and provides cushion/lubrication, increased slippage, and a sheen of the composition when applied to the skin. Dimethicone is present in an amount ranging from 0.1% to 2%, or from 0.2% to 1.5%, or from 0.3% to 1.25% by weight of the composition. The amount can also range from 0.1%, or 0.2%, or 0.3% to 1.25%, or 1.5%, or 2% by weight of the composition. In one instance, the composition includes 0.4% dimethicone by weight. In another instance, the composition includes 0.7% dimethicone by weight. In a further instance, the composition includes 1% dimethicone by weight. In a particular instance, the dimethicone has a viscosity of 10 cst.

A blend of dimethicone and dimethiconol may be included to reduce stickiness and provide cushion/lubrication, increased slippage, and a sheen of the composition when applied to the skin. Such a blend may be included in an amount ranging from 0.025% to 0.2%, or from 0.05% to 0.15%, or from 0.075% to 0.13% by weight of the composition. The amount can also range from 0.025%, or 0.05%, or 0.075% to 0.13%, or 0.15%, or 0.2% by weight of the composition. In one instance, the composition includes 0.1% of such a blend by weight.

Phenyl trimethicone may be included to reduce stickiness and provide cushion/lubrication, increased slippage, and a sheen of the composition when applied to the skin. In one instance, phenyl trimethicone may be included in an amount ranging from 0.08% to 1.1%, or from 0.15% to 0.85%, or from 0.25% to 0.7% by weight of the composition. The amount can also range from 0.08%, or 0.15%, or 0.25% to 0.7%, or 0.85%, or 1.1% by weight of the composition. In another instance, phenyl trimethicone may be included in an amount of 0.35% by weight of the composition. In a further instance, phenyl trimethicone may be included in an amount of 0.55% by weight of the composition.

The composition may include combinations of the above silicones.

Aluminum Starch Octenylsuccinate

The composition includes aluminum starch octenylsuccinate for reducing stickiness of the composition against the surface of skin. Aluminum starch octenylsuccinate is present in an amount ranging from 0.15% to 2%, or from 0.35% to 1.5%, or from 0.55% to 1.25% by weight of the composition. The amount can also range from 0.15%, or 0.35%, or 0.55% to 1.25%, or 1.5%, or 2% by weight of the composition. In one instance, the composition includes 0.75% aluminum starch octenylsuccinate by weight. In another instance, the composition includes 1% aluminum starch octenylsuccinate by weight.

Antioxidants

The composition includes a plurality of antioxidants for reducing dryness and inflammation of the surface of skin. Such antioxidants include a blend of water, pentylene glycol, lecithin, alcohol, ascorbyl palmitate, and tocopherol (the latter two forming a vitamin C and vitamin E complex). Ascorbyl palmitate is a stable form of vitamin C for hydrating, reducing inflammation, and improving tone and texture of the surface of skin. Tocopherol is vitamin E, which reduces dryness and flaking of the surface of skin. Such a blend is present in an amount ranging from 0.0025% to 0.02%, or from 0.005% to 0.015%, or from 0.0075% to 0.013% by weight of the composition. The amount can also range from 0.0025%, or 0.005%, or 0.0075% to 0.013%, or 0.015%, or 0.02% by weight of the composition. In one instance, the composition includes 0.01% of such a blend by weight.

pH-Adjuster

The composition may include a pH-adjuster for neutralizing a pH of said composition. In one instance, the pH-adjuster is sodium hydroxide, and more specifically, sodium hydroxide 50% NF (50% sodium hydroxide, 50% water, National Formulary). Sodium hydroxide also reacts with stearic acid, as described previously, to form sodium stearate. Sodium hydroxide may be included in an amount ranging from 0.01% to 0.1%, or from 0.02% to 0.06%, or from 0.03% to 0.05% by weight of the composition. The amount can also range from 0.01%, or 0.02%, or 0.03% to 0.05%, or 0.06%, or 0.1% by weight of the composition. In one instance, the composition includes 0.04% sodium hydroxide by weight.

Cetearyl Alcohol

The composition may include cetearyl alcohol for increasing a viscosity of emulsion formation of the composition. Cetearyl alcohol may be included in an amount ranging from 0.06% to 0.5%, or from 0.1% to 0.4%, or from 0.15% to 0.35% by weight of the composition. The amount can also range from 0.06%, or 0.1%, or 0.15% to 0.35%, or 0.4%, or 0.5% by weight of the composition. In one instance, the composition includes 0.25% cetearyl alcohol by weight.

D-Panthenol

The composition may include D-panthenol for reducing oxidative stress of the surface of skin. D-panthenol may be included in an amount ranging from 0.1% to 1%, or from 0.2% to 0.6%, or from 0.3% to 0.5% by weight of the composition. The amount can also range from 0.1%, or 0.2%, or 0.3% to 0.5%, or 0.6%, or 1% by weight of the composition. In one instance, the composition includes 0.4% D-panthenol by weight.

Fragrance

In an embodiment, the composition includes a fragrance, for providing an aesthetic scent to the composition. The fragrance may be present in an amount ranging from 0.035% to 1%, or from 0.075% to 0.6%, or from 0.1% to 0.5% by weight of the composition. The amount can also range from 0.035%, or 0.075%, or 0.1% to 0.5%, or 0.6%, or 1% by weight of the composition. In one instance, the composition includes 0.15% fragrance by weight. In another instance, the composition includes 0.25% fragrance by weight. In a further instance, the composition includes 0.4% fragrance by weight. The fragrance is compatible for use with skin and is compatible with the other ingredients of the composition.

Antimicrobial Agents

The composition includes at least one antimicrobial agent for disrupting a microbial cell when in contact with the composition. The microbial cell has a cell membrane encompassed by a cell wall. The at least one antimicrobial agent disrupts the microbial cell by interfering with the cell wall and the cell membrane. This allows for killing of the microbial cell. In an embodiment, the at least one antimicrobial agent is a plurality of antimicrobial agents. In one instance, the plurality of antimicrobial agents includes a blend of phenoxyethanol (a preservative), caprylhydroxamic acid (a chelating agent and potentiator), methylpropanediol (a solvent and potentiator), and water (a carrier for the antimicrobial agents). Phenoxyethanol is a broad-spectrum preservative provided in a synergistic mixture with two different types of potentiators, i.e., caprylhydroxamic acid and methylpropanediol. For the purpose of this application, a "potentiator" is defined as an agent that enhances effectiveness of a preservative in ways such as (but not limited to) chelation and solvency. Caprylhydroxamic acid (octanoyl-hydroxamic acid) is a chelating agent that binds to metal ions on the cell wall of the microbial cell, thereby weakening the cell wall. Caprylhydroxamic acid is also known for disrupting the cell membrane, thus allowing for killing of the microbial cell. Methylpropanediol is a solvent that solubilizes preservatives and chelating agents to allow for increased penetration through the cell wall. This is believed to allow to access the cell membrane, in turn allowing for killing of the microbial cell. The at least one antimicrobial agent or the plurality of antimicrobial agents is present in an amount ranging from 0.1% to 1%, or from 0.25% to 0.75%, or from 0.35% to 0.65% by weight of the composition. The amount can also range from 0.1%, or 0.25%, or 0.35% to 0.65%, or 0.75%, or 1% by weight of the composition. In one instance, the composition includes 0.5% of the at least one antimicrobial agent, or the plurality of antimicrobial agents, by weight. In a particular instance, the blend includes 2-phenoxyethanol and 2-methyl-1,3-propanediol.

In one instance, the blend includes 70% phenoxyethanol, 15% caprylhydroxamic acid, 7.5% methylpropanediol, and 7.5% water.

In one instance, a ratio of phenoxyethanol to caprylhydroxamic acid is 14:3.

In one instance, a ratio of phenoxyethanol to methylpropanediol is 28:3.

In one instance, a ratio of caprylhydroxamic acid to methylpropanediol is 2:1.

In one instance, a ratio of glycerin to the at least one antimicrobial agent ranges from 1.5:1 to 160:1. In another instance, the ratio is 12:1. In a further instance, the ratio is 16:1.

In one instance, a ratio of stearic acid to the at least one antimicrobial agent ranges from 0.06:1 to 5:1. In another instance, the ratio is 0.5:1.

In one instance, a ratio of dimethicone to the at least one antimicrobial agent ranges from 0.1:1 to 20:1. In another instance, the ratio is 0.8:1. In a further instance, the ratio is 1.4:1. In yet another instance, the ratio is 2:1.

In one instance, a ratio of aluminum starch octenylsuccinate to the at least one antimicrobial agent ranges from 0.15:1 to 20:1. In another instance, the ratio is 1.5:1. In a further instance, the ratio is 2:1.

In one instance, a ratio of the at least one antimicrobial agent to the plurality of antioxidants ranges from 5:1 to 400:1. In another instance, the ratio is 50:1.

Alternatively, the at least one antimicrobial agent can include phenoxyethanol, caprylhydroxamic acid, and methylpropanediol each added separately into the overall composition.

Sodium Gluconate

The composition includes sodium gluconate as a micropreservative potentiator, for weakening (by binding to metal ions of) the cell wall of the microbe in contact with the composition, thereby disrupting and even killing the microbe. As above, a "potentiator" is defined as an agent that enhances effectiveness of a preservative in ways such as (but not limited to) chelation and solvency. Sodium gluconate is present in an amount ranging from 0.025% to 0.2%, or from 0.05% to 0.15%, or from 0.075% to 0.13% by weight of the composition. The amount can also range from 0.025%, or 0.05%, or 0.075% to 0.13%, or 0.15%, or 0.2% by weight of the composition. In one instance, the composition includes 0.1% sodium gluconate by weight.

In one instance, a ratio of glycerin to sodium gluconate ranges from 7.5:1 to 640:1. In another instance the ratio is 60:1. In a further instance, the ratio is 80:1.

In one instance, a ratio of stearic acid to sodium gluconate ranges from 0.3:1 to 20:1. In another instance, the ratio is 2.5:1.

In one instance, a ratio of dimethicone to sodium gluconate ranges from 0.5:1 to 80:1. In another instance, the ratio is 4:1. In a further instance, the ratio is 7:1. In yet another instance, the ratio is 10:1.

In one instance, a ratio of aluminum starch octenylsuccinate to sodium gluconate ranges from 0.75:1 to 80:1. In another instance, the ratio is 7.5:1. In a further instance, the ratio is 10:1.

In one instance, a ratio of sodium gluconate to the plurality of antioxidants ranges from 1.25:1 to 80:1. In another instance the ratio is 10:1.

In one instance, a ratio of the at least one antimicrobial agent to sodium gluconate ranges from 0.5:1 to 40:1. In another instance, the ratio is 5:1.

Ethylhexyl Isononanoate

The composition includes ethylhexyl isononanoate as an additional emollient for moisturizing the surface of skin. Ethylhexyl isononanoate is present in an amount ranging from 0.5% to 8%, or from 1% to 6%, or from 1.5% to 5%, by weight of the composition. The amount can also range from 0.5%, or 1%, or 1.5% to 5%, or 6%, or 8% by weight of the composition. In one instance, the composition includes 2% ethylhexyl isononanoate by weight. In another instance, the composition includes 4% ethylhexyl isononanoate by weight.

In one instance, a ratio of glycerin to ethylhexyl isononanoate ranges from 0.18:1 to 32:1. In another instance, the ratio is 1.5:1. In a further instance, the ratio is 2:1. In yet another instance, the ratio is 3:1. In yet a further instance, the ratio is 4:1.

In one instance, a ratio of ethylhexyl isononanoate to stearic acid ranges from 1:1 to 134:1. In another instance, the ratio is 8:1. In a further instance, the ratio is 16:1.

In one instance, a ratio of ethylhexyl isononanoate to dimethicone ranges from 0.25:1 to 80:1. In another instance, the ratio ranges from 2:1 to 10:1.

In one instance, a ratio of aluminum starch octenylsuccinate to ethylhexyl isononanoate ranges from 0.018:1 to 4:1. In another instance, the ratio is 0.375:1. In a further instance, the ratio is 0.1875:1. In yet another instance, the ratio is 0.5:1. In yet a further instance, the ratio is 0.25:1.

In one instance, a ratio of ethylhexyl isononanoate to the at least one antimicrobial agent ranges from 0.5:1 to 80:1. In another instance, the ratio is 4:1. In a further instance, the ratio is 8:1.

In one instance, a ratio of ethylhexyl isononanoate to the plurality of antioxidants ranges from 25:1 to 3200:1. In another instance the ratio is 200:1. In a further instance, the ratio is 400:1.

In one instance, a ratio of sodium gluconate to ethylhexyl isononanoate ranges from 0.003:1 to 0.4:1. In another instance, the ratio is 0.025:1. In a further instance, the ratio is 0.05:1.

Hyaluronic Complex

The composition includes a hyaluronic complex, for hydrating the surface of skin. For the purpose of this application, the term "hyaluronic complex" is defined as a chemical entity including both hyaluronic acid (i.e., native hyaluronic acid) and a salt derivative of hyaluronic acid (e.g., sodium salt derivative of hyaluronic acid).

In one instance, the hyaluronic complex includes hyaluronic acid, a salt derivative of hyaluronic acid, and phenoxyethanol. In another instance, the hyaluronic complex includes hyaluronic acid, sodium hyaluronate, and phenoxyethanol. In both of these instances, the components are anhydrous and become subsumed by the water (i.e., the solvent) of the composition. In a further instance, the hyaluronic complex includes a combination of sodium hyaluronate, hyaluronic acid, phenoxyethanol, and water. That is, water is a carrier for the other three components and is part of the hyaluronic complex to be added into the overall composition.

In a specific embodiment, the hyaluronic complex includes a first blend and a second blend. The first blend includes water, sodium hyaluronate, and phenoxyethanol. The second blend includes water, hyaluronic acid, and phenoxyethanol. Both blends serve to retain water to hydrate and plump up the surface of skin. In a particular instance, phenoxyethanol in both blends is 2-phenoxyethanol.

The blend of water, sodium hyaluronate, and phenoxyethanol (henceforth, blend (i)) is present in an amount ranging from 0.0025% to 0.02%, or from 0.005% to 0.015%, or from 0.0075% to 0.013% by weight of the composition. The amount can also range from 0.0025%, or 0.005%, or 0.0075% to 0.013%, or 0.015%, or 0.02% by weight of the composition. In one instance, the composition includes 0.01% of such a blend by weight.

In one instance, blend (i) includes 98.5% water, 1% sodium hyaluronate, and 0.5% phenoxyethanol by weight of blend (i). A ratio of sodium hyaluronate to phenoxyethanol within blend (i) is 2:1. An example of this is Hyaclear® Solution by TRI-K Industries, Inc.

The blend of water, hyaluronic acid, and phenoxyethanol (henceforth, blend (ii)) is present in an amount ranging from 0.0025% to 0.02%, or from 0.005% to 0.015%, or from 0.0075% to 0.013% by weight of the composition. The amount can also range from 0.0025%, or 0.005%, or 0.0075% to 0.013%, or 0.015%, or 0.02% by weight of the composition. In one instance, the composition includes 0.01% of such a blend by weight.

In one instance, blend (ii) includes 98% water, 1% hyaluronic acid, and 1% phenoxyethanol. A ratio of hyaluronic acid to phenoxyethanol within blend (ii) is 1:1. An example of this is made by Draco Natural Products, Inc.

The hyaluronic complex is present in an amount ranging from 0.005% to 0.04%, or from 0.01% to 0.03%, or from 0.015% to 0.025% by weight of the composition. The amount can also range from 0.005%, or 0.01%, or 0.015% to 0.025%, or 0.03%, or 0.04% by weight of the composition. In one instance, the composition includes 0.02% of the hyaluronic complex by weight.

In one instance, a ratio of sodium hyaluronate to total phenoxyethanol within the hyaluronic complex is 2:3.

In one instance, a ratio of hyaluronic acid to total phenoxyethanol within the hyaluronic complex is 2:3.

In one instance, a ratio of sodium hyaluronate to hyaluronic acid is 1:1.

In one instance, a ratio of blend (i) to blend (ii) is 1:1.

In one instance, a ratio of sodium gluconate to blend (i) ranges from 1.25:1 to 80:1. In another instance, the ratio is 10:1.

In one instance, a ratio of sodium gluconate to blend (ii) ranges from 1.25:1 to 80:1. In another instance, the ratio is 10:1.

In one instance, a ratio of sodium gluconate to hyaluronic complex ranges from 0.6:1 to 40:1. In another instance, the ratio is 5:1.

In one instance, a ratio of ethylhexyl isononanoate to blend (i) ranges from 25:1 to 3200:1. In another instance, the ratio is 200:1. In a further instance, the ratio is 400:1.

In one instance, a ratio of ethylhexyl isononanoate to blend (ii) ranges from 25:1 to 3200:1. In another instance, the ratio is 200:1. In a further instance, the ratio is 400:1.

In one instance, a ratio of ethylhexyl isononanoate to hyaluronic complex ranges from 12.5:1 to 1600:1. In another instance, the ratio is 100:1. In a further instance, the ratio is 200:1.

In one instance, a ratio of glycerin to blend (i) ranges from 75:1 to 6400:1. In another instance, the ratio is 600:1. In a further instance, the ratio is 800:1.

In one instance, a ratio of glycerin to blend (ii) ranges from 75:1 to 6400:1. In another instance, the ratio is 600:1. In a further instance, the ratio is 800:1.

In one instance, a ratio of glycerin to hyaluronic complex ranges from 37.5:1 to 3200:1. In another instance, the ratio is 300:1. In a further instance, the ratio is 400:1.

In one instance, a ratio of stearic acid to blend (i) ranges from 3:1 to 200:1. In another instance, the ratio is 25:1.

In one instance, a ratio of stearic acid to blend (ii) ranges from 3:1 to 200:1. In another instance, the ratio is 25:1.

In one instance, a ratio of stearic acid to hyaluronic complex ranges from 1.5:1 to 100:1. In another instance, the ratio is 12.5:1.

In one instance, a ratio of dimethicone to blend (i) ranges from 5:1 to 800:1. In another instance, the ratio is 40:1. In a further instance, the ratio is 70:1. In yet another instance, the ratio is 100:1.

In one instance, a ratio of dimethicone to blend (ii) ranges from 5:1 to 800:1. In another instance, the ratio is 40:1. In a further instance, the ratio is 70:1. In yet another instance, the ratio is 100:1.

In one instance, a ratio of dimethicone to hyaluronic complex ranges from 2.5:1 to 400:1. In another instance, the ratio is 20:1. In a further instance, the ratio is 35:1. In yet another instance, the ratio is 50:1.

In one instance, a ratio of aluminum starch octenylsuccinate to blend (i) ranges from 7.5:1 to 800:1. In another instance, the ratio is 75:1. In a further instance, the ratio is 100:1.

In one instance, a ratio of aluminum starch octenylsuccinate to blend (ii) ranges from 7.5:1 to 800:1. In another instance, the ratio is 75:1. In a further instance, the ratio is 100:1.

In one instance, a ratio of aluminum starch octenylsuccinate to hyaluronic complex ranges from 3.75:1 to 400:1. In another instance, the ratio is 37.5:1. In a further instance, the ratio is 50:1.

In one instance, a ratio of blend (i) to the plurality of antioxidants ranges from 0.1:1 to 8:1. In another instance, the ratio is 1:1.

In one instance, a ratio of blend (ii) to the plurality of antioxidants ranges from 0.1:1 to 8:1. In another instance, the ratio is 1:1.

In one instance, a ratio of hyaluronic complex to the plurality of antioxidants ranges from 0.25:1 to 16:1. In another instance, the ratio is 2:1.

In one instance, a ratio of the at least one antimicrobial agent to blend (i) ranges from 5:1 to 400:1. In another instance, the ratio is 50:1.

In one instance, a ratio of the at least one antimicrobial agent to blend (ii) ranges from 5:1 to 400:1. In another instance, the ratio is 50:1.

In one instance, a ratio of the at least one antimicrobial agent to hyaluronic complex ranges from 2.5:1 to 200:1. In another instance, the ratio is 25:1.

In one instance, the combination of the at least one antimicrobial agent, sodium gluconate, ethylhexyl isononanoate, and hyaluronic complex ranges from 0.6% to 10% by weight of the composition. In another instance, the combination ranges from 2.5% to 5% by weight of the composition. The combination can also range from 0.6% or 2.5% to 5% or 10% by weight of the composition.

Methods of Making

The Inventive Examples (IE's) of the present invention were prepared as follows:

IE1

Water, glycerin, and sodium gluconate were each weighed and added into a mixing vessel to begin a water-phase mixture. Mixing commenced, with the blend of acrylates and $C_{10\text{-}30}$ alkyl acrylate crosspolymer being added slowly into the water-phase mixture and mixed in for 10 minutes to complete polymer hydration. The water-phase mixture at this point was then heated to a temperature ranging from 70° C. to 80° C. (e.g., from 73° C. to 77° C.). Upon reaching the target temperature and complete dissolution of the ingredients thus far, sodium hydroxide 50% NF was then added into the water-phase mixture. For another 20 minutes, the water-phase mixture was then moderately agitated as a dispersion.

In a separate mixing vessel, ethylhexyl isononanoate, the blend of glyceryl stearate and PEG-100 stearate, ceteareth-20, stearic acid, dimethicone, phenyl trimethicone, and cetyl esters wax NF were each weighed and added to begin an oil-phase mixture. The oil-phase mixture at this point was then heated to a temperature ranging from 70° C. to 80° C. (e.g., from 73° C. to 77° C.).

When the oil-phase mixture was completely melted, the water-phase mixture was regularly agitated to form a moderate vortex. Aluminum starch octenylsuccinate was weighed and added into the oil-phase mixture, which was then mixed to become homogeneous. The temperatures of both the water-phase mixture and the oil-phase mixture were then noted, and the oil-phase mixture thus added to the water-phase mixture (forming a combined mixture) until homogeneity was obtained. Speed of mixing was gradually increased during this step (lasting 5 minutes), so as to ensure formation of an emulsion (i.e., a smooth emulsion) while avoiding excessive aeration. Then, the resultant emulsion was removed from heat and air-cooled with moderate agitation.

When the emulsion reached a temperature of 60° C., the blend of: water, polyacrylamide, C13-14 isoparaffin, and laureth-7 was weighed and added to the emulsion. Moderate mixing and air-cooling continued.

The target temperature of the emulsion ranged from 35° to 40° C. (for instance, 38° C.). After 20 minutes of mixing and air-cooling, a cool water bath could optionally be used to expedite cooling.

Once the emulsion achieved target temperature, then the antioxidants, both blends of the hyaluronic complex, the antimicrobial agents, and the fragrance were each weighed and added into the emulsion. These ingredients were mixed in for 5 minutes to form the final composition, IE1.

For IE4, the procedure was identical to that of IE1, with the exclusion of the fragrance.

IE2

The procedure for IE2 was similar to that of IE1, with the following variations:

Butylene glycol was included as part of the water-phase mixture. The blend of acrylates and C10-30 alkyl acrylate crosspolymer was excluded from IE2.

The oil-phase mixture of IE2 was made up of the following: ethylhexyl isononanoate, the blend of caprylic triglyceride and capric triglyceride, the blend of glyceryl stearate and PEG-100 stearate, glyceryl stearate alone, stearic acid, cetearyl alcohol, dicaprylyl ether, isopropyl palmitate, and glyceryl dilaurate. The same process conditions were used as above for IE1, with aluminum starch octenylsuccinate being weighed and added upon complete melting of the oil-phase mixture, until homogeneity obtained.

Similar to IE1 above, the oil-phase mixture was then added to the water-phase mixture to form a combined mixture. Rapid mixing was maintained at 70° C. to 80° C. (e.g., from 73° C. to 77° C.) for 10 minutes. The combined mixture was then cooled, until a target temperature of 60° C. was reached.

Meanwhile, a further mixture was formed by weighing and adding each of dimethicone and the blend of water, sodium acrylate, sodium acryloyldimethyl taurate copolymer, C15-19 alkane, polyglyceryl-6 laurate, and polyglycerin-6. The further mixture was added to the combined mixture upon reaching target temperature of the combined mixture, to form a pre-final mixture.

The pre-final mixture was cooled to 35° C. and homogeneity ensured. Then, both blends of the hyaluronic complex, D-panthenol, the blend of water, xylitylglucoside, anhydroxylitol, and xylitol, the antioxidants, the antimicrobial agents, and the fragrance were each weighed and added to the pre-final mixture. Moderate mixing was maintained for 10 to 15 minutes to form the final composition, IE2.

IE3

The water-phase mixture of IE3 included two pre-mixtures. The first pre-mixture included the same ingredients as that of IE1, with the exception of only having a portion of the total amount of glycerin (i.e., less than half, for instance 3% by weight of the final composition).

The second pre-mixture was formed by weighing and adding: a second portion of the total amount of glycerin (i.e., less than half, for instance 2% by weight of the final composition) and xanthan gum. The second pre-mixture was slowly added to the first pre-mixture to form the water-phase mixture, which was then heated to 70° C. to 80° C. (e.g., from 73° C. to 77° C.). Moderate agitation of the water-phase mixture was maintained until total dissolution of all ingredients was achieved.

An oil-phase mixture of IE3 was formed as follows: ethylhexyl isononanoate, the blend of caprylic triglyceride and capric triglyceride, ceteareth-20, stearic acid, phenyl trimethicone, and cetyl esters wax NF were each weighed and added into a separate mixing vessel and heated to a temperature ranging from 70° C. to 80° C. (e.g., from 73° C. to 77° C.). Once these ingredients were completely melted, shea butter was added and mixed in until homogeneity obtained. Then, aluminum starch octenylsuccinate was added and mixed in until homogeneity obtained.

At this point, the temperatures of both the water-phase mixture and the oil-phase mixture were noted. Then, the oil-phase mixture was added to the water-phase mixture (forming a combined mixture) under rapid mixing at the target temperature.

Meanwhile, a dimethicone-dimethiconol mixture of IE3 was formed by weighing and adding dimethicone and the blend of dimethicone and dimethiconol. The dimethicone-dimethiconol mixture was then added to the combined mixture (forming a pre-final mixture), with rapid mixing maintained for 10 minutes. During this time, the pre-final mixture was cooled to a target temperature of 35° C.

When the pre-final mixture reached target temperature, both blends of the hyaluronic complex, the antimicrobial agents, a remaining portion of the total amount of glycerin (i.e., less than half, for instance 3% by weight of the final composition), sodium acrylates crosspolymer-2, the antioxidants, and the fragrance were each weighed and added to the pre-final mixture. Mixing then occurred for 10 to 15 minutes to form the final composition, IE3.

Method of Use

As a general, non-limiting example of a method of use for the composition, a user releases the composition from its packaging onto one's hand. This may be, for instance, squeezing from a tube, pumping from a bottle, or scooping from a jar. The amount of the composition used will vary from one user to another, but can range, for instance, from 0.25 g to 20 g, or from 0.5 g to 15 g, or from 1 g to 10 g, or from 2 g to 8 g, or from 5 g to 7 g. Once in hand, the composition is rubbed into the surface of skin until no longer visible. The composition can be applied to a portion of the user (e.g., hands, feet, legs, or arms), or one's entire body.

Highlights of Formulation Development

A major goal of the work done for the present invention was to create a composition, for application to a surface of skin, that is free (i.e., containing 0%) of ingredients including: parabens, BHT, petrolatum, and dyes, while still providing the desired benefits stated in the Background section. This is not meant to be an exhaustive list of excluded ingredients. The work described herein focuses on the components believed to contribute to the features and benefits of the Inventive Examples.

Experimentation with various ingredients was performed, with the intent of obtaining a gel cream. Four test formulations, shown in Table 1 below, were created after completion of initial experimentation and sensory evaluation.

TABLE 1

Compositions of Initial Test Formulations (*total of 2 different viscosity types)

| Ingredient | Test Formulation 1 | Test Formulation 2 | Test Formulation 3 | Test Formulation 4 |
|---|---|---|---|---|
| Water (Aqua) | 82.7498 | 81.1399 | 80.8612 | 83.1 |
| Glycerin | 6 | 10 | 10 | |
| Ethylhexylglycerin/Water (Aqua) | 0.4 | | | 0.4 |
| Disodium EDTA | 0.1 | | | |
| Acrylates/$C_{10-30}$ Alkyl Acrylate Crosspolymer | 0.1 | | 1.2 | |
| Blue 1/Cl 42090/Acid Blue 9 | 0.0002 | 0.0001 | 0.0002 | |
| Sodium Hydroxide/Water (Aqua) | 0.04 | | | |
| Ethylhexyl Isononanoate | 4 | | | |
| Glyceryl Stearate/PEG-100 Stearate | 1 | | | |
| Ceteareth-20 | 0.25 | | | |
| Stearic Acid | 0.25 | | | |
| Dimethicone | 0.5 | 5.5* | 6 | |
| Phenyl Trimethicone | 1 | | | 4 |
| Tocopheryl Acetate | 0.01 | | | |
| Cetyl Esters | 0.25 | | | |
| Aluminum Starch Octenylsuccinate | 1 | | | |
| Polyacrylamide/Laureth-7/$C_{13-14}$ Isoparaffin/Water (Aqua) | 1.5 | | | |
| Caprylyl Glycol | 0.24 | | | |
| Water (Aqua)/Sodium Hyaluronate/Phenoxyethanol | 0.01 | 0.01 | 0.01 | |
| Phenoxyethanol | 0.4 | 0.15 | 0.15 | 0.4 |
| Fragrance | 0.2 | 0.3 | 0.3 | 0.2 |
| Methylparaben | | 0.2 | 0.2 | |
| Ethylparaben | | 0.1 | 0.1 | |
| Hydroxyethyl Acrylate/Sodium Acryloyldimethyl Taurate Copolymer/Water (Aqua)/Isohexadecane/Polysorbate 60 | | 2 | | |
| Xanthan Gum | | 0.1 | 0.1 | |
| Hexylene Glycol | | 0.5 | 0.5 | |
| Hydroxyethyl Acrylate/Sodium Acryloyldimethyl Taurate Copolymer | | | 0.1786 | |
| Ceteareth-25 | | | 0.4 | |
| Butylene Glycol | | | | 6 |
| Sodium Acrylate/Sodium Acryloyldimethyl Taurate Copolymer and $C_{15-19}$ Alkane and Polyglyceryl-6 Laurate (and water) | | | | 2.5 |
| D-Panthenol | | | | 0.4 |
| Xylitylglucoside and Anhydroxylitol and Xylitol (and water) | | | | 3 |
| Total | 100 | 100 | 100 | 100 |

It is noted that only Test Formulation 1 included both ethylhexyl isononanoate and blend (i) of the hyaluronic complex. At this point in development, these components were included for their known functions as described above. However, they were together in Test Formulation 1 based solely on initial sensory evaluation of the test formulations, and not for any expected synergy.

An internally-conducted Home Use Test (HUT) was carried out. For the HUT, 17 females, aged 20-44 years old, did a full-body application of each test formulation at least once a day, over two days. While all four test formulations were included in the HUT, only Test Formulations 1 and 2 were in targeted product form, i.e., a gel cream. A comparison of Test Formulations 1 and 2 in Table 2 below summarizes several of the various aspects that each panelist was asked to describe for each test formulation.

TABLE 2

Highlights of Questionnaire and
Comparison of Test Formulations 1 and 2

| Aspect | Test Formulation 1 | Test Formulation 2 |
|---|---|---|
| Overall, do you like product? (Yes) | 82% | 76% |
| Better than/same as your current body moisturizer? (Yes) | 65% | 59% |
| Do you like consistency of formulation? (Yes) | 76% | 82% |
| Acceptable speed of absorption into skin (Yes) | 88% | 71% |
| Comfortable feel of formulation? (Yes) | 71% | 82% |
| Comfortable moisturization? (Yes) | 47% | 53% |
| Comfortable hydration? (Yes) | 76% | 59% |

Panelists were asked to detail the reasons for their preference for either test formulation. In general, Test Formulation 1 was preferred because its consistency was thin yet firm (i.e., not too watery) and more closely resembled that of a typical lotion, while providing a positive user experience. Again, only Test Formulation 1 included both ethylhexyl isononanoate and blend (i) of the hyaluronic complex. Thus, Test Formulation 1 already included two components that were to eventually become part of the combination of components believed to provide the features and benefits observed in the final formulations that are the Inventive Examples. At this early stage in development, it was not yet known or expected that such features and benefits would arise. Test Formulation also included many other ingredients not included Test Formulation 2 (as shown in Table 1) that eventually became part of the final formulation. Furthermore, Test Formulation 1 excluded ingredients such as parabens, BHT, petrolatum, and dyes.

Hyaluronic acid, known for retaining water to provide hydration to skin, was added in the form of blend (ii) of the hyaluronic complex. While blend (ii) was added for its known function, it was not known or expected that the features and benefits observed in the Inventive Examples would arise as a result of the believed synergy between the at least one antimicrobial agent, sodium gluconate, ethylhexyl isononanoate, and the hyaluronic complex.

Multiple preservative systems were tested for inclusion in the composition. For the purpose of this application, the term "preservative system" is defined as a combination of chemical moieties for disrupting a microbial cell. Preservative Efficacy Testing (PET) was completed using a modified version of the ISO 11930 method at different points during formulation development. The modification included a proprietary blend of microorganisms in conjunction with accelerated stability to stress the formulation and the preservative system. PET is an essential part of product safety substantiation and demonstrates protection against the presence of microorganisms during normal consumer usage.

At this point, the formulations of the Inventive Examples were finalized, with only the preservative system remaining to be determined. As demonstrated in Table 3 below, five different preservative systems were tested for their efficacy with three of the Inventive Examples (IE1-IE3). To be acceptable for use, the sample must meet success criteria of PET at time=0 through 4.5 months under accelerated conditions.

In Table 3 below, SymOcide® PH is by Symrise, Microcare® PHDG2 is by Thor, and Phenostat™ is by Inolex.

TABLE 3

Results of Preservative Efficacy Testing

| Preservative System | IE1 | IE2 | IE3 |
|---|---|---|---|
| SymOcide ® PH + Sodium Gluconate | Failed initial test on lab sample | Passed 4.5 month accelerated stability and test on lab sample | Not Tested |
| MICROCARE ® PHDG2 + Sodium Gluconate | Failed initial test on lab sample | Not Tested | Passed 4.5 month accelerated stability and test on lab sample |
| Phenostat ™ + Sodium Gluconate | Passed 4.5 month accelerated stability and test on lab, pilot, and plant trial samples | Passed 4.5 month accelerated stability and test on lab, pilot, and plant trial samples | Passed 4.5 month accelerated stability and test on lab, pilot, and plant trial samples |
| Sodium Benzoate + Phenoxyethanol + Sodium Gluconate | *Passed 4.5 month accelerated stability and test on lab sample | Not Tested | Not Tested |
| SymOcide ® PH (increased level) + Sodium Gluconate | Passed 3 month accelerated stability and test on lab sample | Not Tested | Not Tested |

*Sample was runny, which may have affected results. No further testing.

As is evident from Table 3, only the combination of Phenostat™ and sodium gluconate passed all testing up to 4.5 accelerated months for IE1-IE3. Phenostat™ is a blend of phenoxyethanol, caprylhydroxamic acid, methylpropanediol, and water. This of course is the blend, or the plurality, of antimicrobial agents described previously. Thus, the at least one antimicrobial agent and sodium gluconate proved to be effective as a preservative system for the Inventive Examples.

The combination of the at least one antimicrobial agent, sodium gluconate, ethylhexyl isononanoate, and the hyaluronic complex is common to all Inventive Examples. This combination does not appear to be present in the Comparative Samples named below, or the references stated in the Background Section. Further testing was done on the Inventive Examples to determine their properties, as discussed below.

Properties of and Benefits Provided by the Present Composition

Bound by no particular theory, it is believed that the combination of the at least one antimicrobial agent, sodium gluconate, ethylhexyl isononanoate, and the hyaluronic complex may contribute to the properties demonstrated by the composition in comparison to current commercialized formulations. Specifically, this combination may work with the rest of the ingredients to provide benefits including, but not limited to, lower friction and increased breathability to the composition when applied to the surface of skin. In particular, this combination may work with ingredients such as glycerin, stearic acid, dimethicone/the plurality of silicones, aluminum starch octenylsuccinate, and the plurality of antioxidants by enhancing their respective functions. For instance, it is possible that the function of aluminum starch octenylsuccinate, which is to reduce stickiness of the composition against the surface of skin, may be augmented by this combination. Likewise, it is possible that the function of dimethicone/the plurality of silicones, which is to provide lubrication and reduce stickiness of the composition upon application to the surface of skin, may be also be augmented by this combination. Furthermore, the composition has such a combination with such properties while excluding ingredients such as parabens, BHT, petrolatum, and dyes.

Table 4 below shows complete ingredient listings of three Inventive Examples (IE1-IE3), which are embodiments of the composition. A fourth Inventive Example, IE4, was also created as a fragrance-free alternative to IE1, and is a further embodiment of the composition. That is, IE4 is basically IE1 minus fragrance. However, all other ingredients of IE4 remain the same as those of IE1. IE4 was not included in any testing. The amounts of each ingredient are shown for the Inventive Examples, as a percentage by weight of the entire composition. Tables 5-8 show ingredient listings of multiple Comparative Samples (CS1-CS11). The Comparative Samples were included in various tests to provide a reference point for the Inventive Examples. The Comparative Samples are all current commercialized products.

TABLE 4

Composition of Inventive Examples

| Ingredient | IE1 | IE2 | IE3 | IE4 |
|---|---|---|---|---|
| Deionized Water | 83.78 | 78.51 | 80.17 | 84.03 |
| Glycerin (vegetable grade) | 6 | 6 | 8 | 6 |
| Xylitylglucoside and Anhydroxylitol and Xylitol (and water) | | 1 | | |
| Butylene Glycol | | 3 | | |
| Xantham Gum | | | 0.2 | |
| Sodium Gluconate | 0.1 | 0.1 | 0.1 | 0.1 |
| Acrylates/C$_{10-30}$ Alkyl Acrylate Crosspolymer | 0.1 | | | 0.1 |
| Sodium Hydroxide (50%) NF | 0.04 | | | 0.04 |
| Ethylhexyl Isononanoate | 4 | 2 | 4 | 4 |
| Caprylic/Capric Triglyceride | | 1 | 1 | |
| Glyceryl Stearate and PEG-100 Stearate | 0.9 | 0.03 | | 0.9 |
| Glyceryl Stearate | | 0.03 | | |

TABLE 4-continued

Composition of Inventive Examples

| Ingredient | IE1 | IE2 | IE3 | IE4 |
|---|---|---|---|---|
| Ceteareth-20 | 0.25 | | 0.25 | 0.25 |
| Stearic Acid (vegetable grade) | 0.25 | 0.25 | 0.25 | 0.25 |
| Dimethicone (10 cst) | 0.7 | 1 | 0.4 | 0.7 |
| Dimethicone and Dimethiconol | | | 0.1 | |
| Phenyl Trimethicone | 0.35 | | 0.55 | 0.35 |
| Cetearyl Alcohol | | 0.25 | | |
| Dicaprylyl Ether | | 0.5 | | |
| Cetyl Esters Wax NF | 0.25 | | 0.25 | 0.25 |
| Isopropyl Palmitate | | 1 | | |
| Glyceryl Dilaurate | | 1 | | |
| Butyrospermum Parkii (Shea) Butter | | | 2 | |
| Aluminum Starch Octenylsuccinate | 1 | 0.75 | 1 | 1 |
| Sodium Acrylate/Sodium Acryloyldimethyl Taurate Copolymer and C$_{15-19}$ Alkane and Polyglyceryl-6 Laurate and Polyglycerin-6 (and water) | | 2.5 | | |
| Polyacrylamide and C$_{13-14}$ Isoparaffin and Laureth-7 (and water) | 1.5 | | | 1.5 |
| Sodium Acrylates Crosspolymer-2 | | | 0.8 | |
| D-Panthenol | | 0.4 | | |
| Water and Pentylene Glycol and Lecithin and Alcohol and Ascorbyl Palmitate and Tocopherol | 0.01 | 0.01 | 0.01 | 0.01 |
| Water and Sodium Hyaluronate and Phenoxyethanol | 0.01 | 0.01 | 0.01 | 0.01 |
| Water and Hyaluronic Acid and Phenoxyethanol | 0.01 | 0.01 | 0.01 | 0.01 |
| Phenoxyethanol, Caprylhydroxamic Acid, Methylpropanediol, Water/Aqua | 0.5 | 0.5 | 0.5 | 0.5 |
| Fragrance | 0.25 | 0.15 | 0.4 | |

TABLE 5

Composition of Comparative Samples 1-3

| Ingredient | Nivea ® Breathable Nourishing Body Lotion (CS1) | Jergens ® Ultra Healing (CS2) | Neutrogena ® Hydro Boost Body Gel Cream (CS3) |
|---|---|---|---|
| Water | X | X | X |
| Glycerin | X | X | X |
| Acrylates/C$_{10-30}$ Alkyl Acrylate Crosspolymer | X | | |
| Sodium Hydroxide | X | X | X |
| Ceteareth-20 | | X | |
| Stearic Acid | | X | |
| Dimethicone | X | X | X |
| Cetearyl Alcohol | | X | |
| Isopropyl Palmitate | X | | X |
| Butyrospermum Parkii (Shea) Butter | X | | |
| Aluminum Starch Octenylsuccinate | | X | |
| Panthenol | X | X | |

TABLE 5-continued

Composition of Comparative Samples 1-3

| Ingredient | Nivea ® Breathable Nourishing Body Lotion (CS1) | Jergens ® Ultra Healing (CS2) | Neutrogena ® Hydro Boost Body Gel Cream (CS3) |
|---|---|---|---|
| Pentylene Glycol and Lecithin and Alcohol and Ascorbyl Palmitate and Tocopherol | | X | |
| Fragrance | X | X | X |
| $C_{12-15}$ Alkyl Benzoate | X | X | |
| Behenyl Alcohol | X | | |
| Glycine Soja (Soybean) Oil | X | | |
| PPG-15 Stearyl Ether | X | | |
| Ethylhexylglycerin | X | | X |
| Benzoic Acid | X | | |
| BHT | X | | |
| Petrolatum | | X | X |
| Laureth-3 | | X | |
| Allantoin | | X | |
| Arginine | | X | |
| Carbomer | | X | X |
| Methylparaben | | X | |
| Ethylparaben | | X | |
| Cetearyl Olivate | | | X |
| Caprylyl Glycol | | | X |
| Sorbitan Olivate | | | X |
| Blue 1 | | | X |
| Cetyl Alcohol | | | X |
| Phenoxyethanol | X | X | X |
| Tocopherol | X | | |
| Sodium Hyaluronate | | | X |
| Sodium Polyacrylate | | | X |

TABLE 6

Composition of Comparative Samples 4-6

| Ingredient | Neutrogena ® Hydro Boost Hand Gel Cream (CS4) | Neutrogena ® Hydro Boost Whipped Body Balm (CS5) | Petrolatum (Regent White Pet USP) (CS6) |
|---|---|---|---|
| Water | X | X | |
| Glycerin | X | X | |
| Xanthan Gum | | X | |
| Sodium Hydroxide | X | X | |
| Dimethicone | X | X | |
| Isopropyl Palmitate | X | X | |
| Sodium Acrylates Crosspolymer-2 | | X | |
| Fragrance | X | X | |
| Ethylhexylglycerin | X | X | |
| BHT | | | X |
| Petrolatum | X | X | X |
| Carbomer | X | X | |
| Cetearyl Olivate | X | X | |
| Caprylyl Glycol | X | | |
| Sorbitan Olivate | X | X | |
| Blue 1 | X | X | |
| Cetyl Alcohol | X | X | |
| Phenoxyethanol | X | X | |
| Sodium Polyacrylate | X | | |
| Sodium Hyaluronate | X | X | |

TABLE 7

Composition of Comparative Samples 7-8

| Ingredient | Jergens ® Soothing Aloe Moisturizer (CS7) | Jergens ® Shea Butter Moisturizer (CS8) |
|---|---|---|
| Water | X | X |
| Glycerin | X | X |
| Butylene Glycol | X | |
| Acrylates/$C_{10-30}$ Alkyl Acrylate Crosspolymer | X | |
| Sodium Hydroxide | X | X |
| Glyceryl Stearate | X | |
| Ceteareth-20 | X | X |
| Stearic Acid | X | X |
| Dimethicone | X | X |
| Cetearyl Alcohol | X | X |
| Cetyl Esters | X | X |
| Butyrospermum Parkii (Shea) Butter | | X |
| Fragrance | X | X |
| Petrolatum | | X |
| Allantoin | X | |
| Arginine | X | X |
| Carbomer | | X |
| Methylparaben | X | X |
| Ethylparaben | X | X |
| Cetyl Alcohol | X | |
| Hydrogenated Vegetable Oil | X | |
| Isopropyl Myristate | X | |
| Canola Oil | X | |
| Propylene Glycol | X | |
| Sodium PCA | X | |
| Aloe barbadensis Leaf Extract | X | |
| Eucalyptus globulus Leaf Extract | X | |
| Cucumis sativus Fruit Extract | X | |
| Octyldodecyl Myristate | | X |
| Hydroxyethyl Urea | | X |
| Hydrogenated Polydecene | | X |
| Mineral Oil | | X |
| Ethylhexyl Isononanoate | | X |
| Magnifera indica Seed Butter | | X |
| Theobroma cacao Seed Butter | | X |
| Tocopheryl Acetate | | X |
| Caramel | | X |
| Phenoxyethanol | X | X |

TABLE 8

Composition of Comparative Samples 9-11

| Ingredient | Nivea ® Essentially Enriched (CS9) | Eucerin ® Original Healing (CS10) | Vaseline ® Petroleum Jelly (CS11) |
|---|---|---|---|
| Water | X | X | |
| Glycerin | X | | |
| Isopropyl Palmitate | | X | |
| Fragrance | X | | X |
| Petrolatum | X | | White Petrolatum USP 99.96% |
| Propylene Glycol | | X | |
| Mineral Oil | X | X | |
| Isohexadecane | X | | |
| PEG-40 Sorbitan Perisostearate | X | | |
| Prunus amygdalus dulcis Oil | X | | |
| Magnesium Sulfate | X | X | |
| Citric Acid | X | X | |
| Sodium Citrate | X | X | |
| Potassium Sorbate | X | X | |
| Sorbitol | | X | |
| Diisostearoyl Polyglyceryl-3 Dimer Dilinoleate | | X | |

TABLE 8-continued

Composition of Comparative Samples 9-11

| Ingredient | Nivea ® Essentially Enriched (CS9) | Eucerin ® Original Healing (CS10) | Vaseline ® Petroleum Jelly (CS11) |
|---|---|---|---|
| Polyglyceryl-4 Diisostearate/ Polyhydroxystearate/Sebacate | | X | |
| Cetyl Palmitate | | X | |
| Aluminum Stearates | | X | |
| Lanolin Alcohol | | X | |
| Phenoxyethanol | | X | X |

Data

For all except barrier efficacy data, 12 candidates participated, aged 18-45 years old, who identified themselves as having normal or dry skin. The candidates were not allowed to have any of the following criteria:

1. Pregnant, nursing, or actively trying to become pregnant.
2. Illnesses or diseases which might interfere with the conduct of the study or the interpretation of results.
3. Prescription medication which might interfere with the conduct of the study or the interpretation of results.
4. Topical antibiotic on their skin two weeks prior to the study.
5. Any skin condition or disease on their hand or body skin, or under the care of a doctor or dermatologist for such a condition or disease.
6. Known sensitivity or allergy to any body or hand care product, or to any specific ingredient, fragrance or dye used in these types of products.
7. Currently participating in any other clinical or consumer study on the body or hand, or any other study that might interfere with the conduct of the study or the interpretation of results.

Candidates were not allowed to use any moisturizing products on both left and right forearms on the morning of testing and had to bathe/shower no later than two hours before testing. Hot beverages were not to be consumed one hour before, and during, the test. Candidates were also required to wear sleeves that could be easily rolled up to expose the forearms.

Three test sites on each forearm (for a total of six test sites), each measuring 4 cm×5 cm, were marked on each forearm, as depicted in FIG. 1. A first and a fourth of the six test sites were marked near a respective wrist of a forearm (avoiding bony areas of the wrists). A second and a fifth of the six test sites were marked along a respective length of a forearm. A third and a sixth of the six test sites were marked near a respective elbow of a forearm. One test site remained untreated. The other five test sites were treated separately with one of: IE1-IE3, petrolatum, or Nivea® Breathable Nourishing Body Lotion. Each treated test site received 40 µL (2.0 mg/cm$^3$) of a respective formulation, via rubbing the formulation from a finger into the test site for 30 seconds. Treatments were done one by one and were randomized (i.e., the untreated test site was different among the candidates, as was placement of each formulation) to avoid bias.

Friction

Figure 2A:
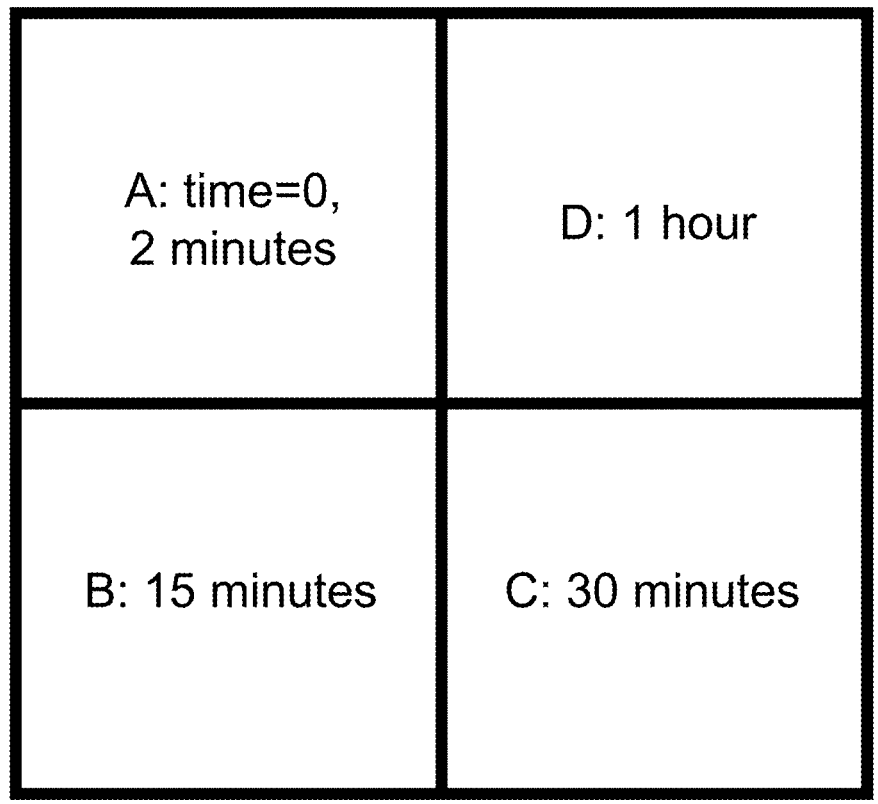
FIG. 2A illustrates a test site divided into four sub-sites for obtaining friction data.

An FR700 friction meter (manufactured by Courage+ Khazaka) was used for obtaining friction data. As indicated in FIG. 2A, each test site was divided into four sub-sites, A-D that were then measured with a probe having a round surface to contact the skin. Sub-site A was measured at both baseline (time=0) and 2 minutes. Sub-site B was measured at 15 minutes. Sub-site C was measured at 30 minutes. Sub-site D was measured at 1 hour.

Figure 2B:
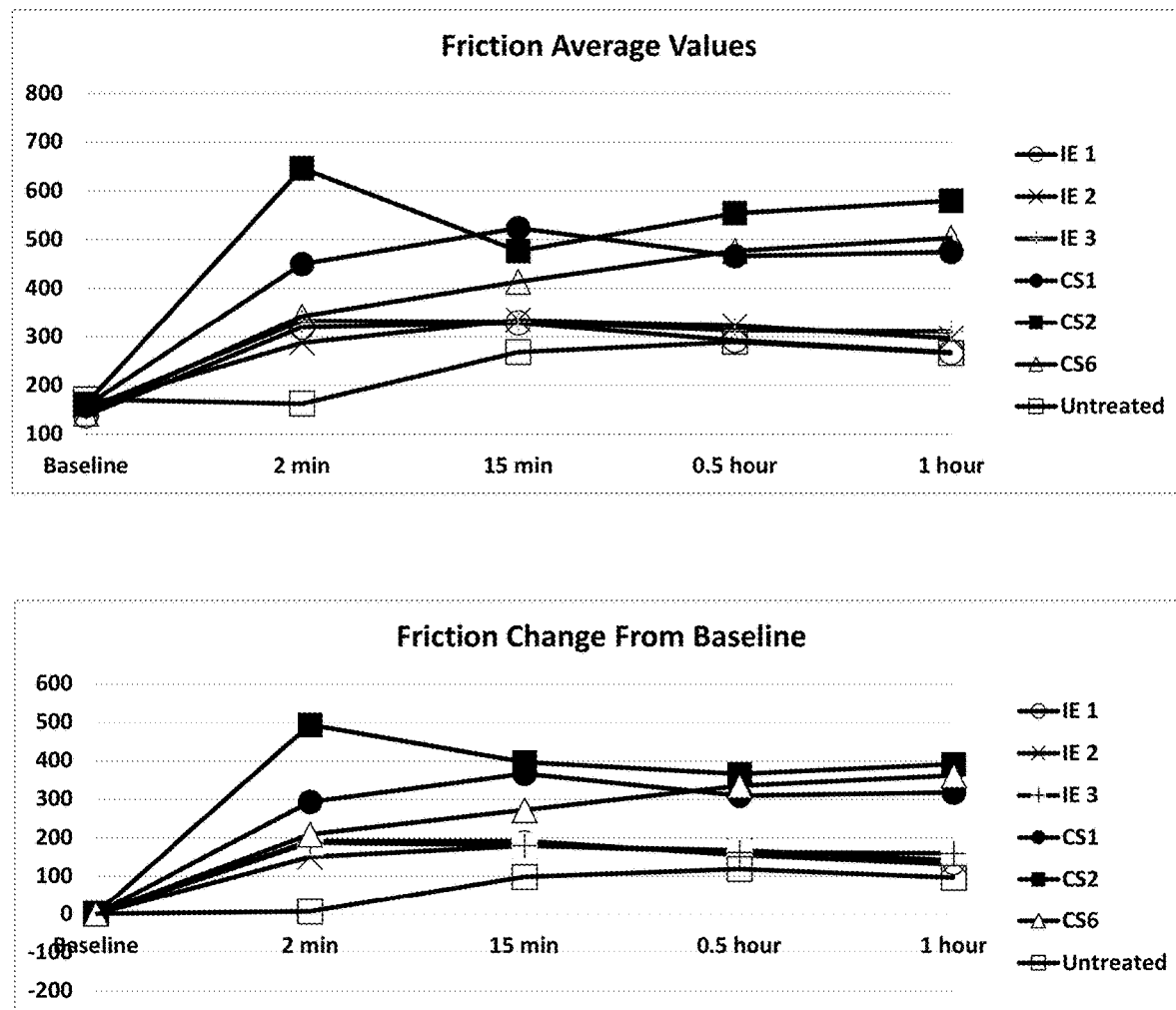
FIG. 2B depicts friction data of Inventive Examples vs. Comparative Samples.
Figure 2C:
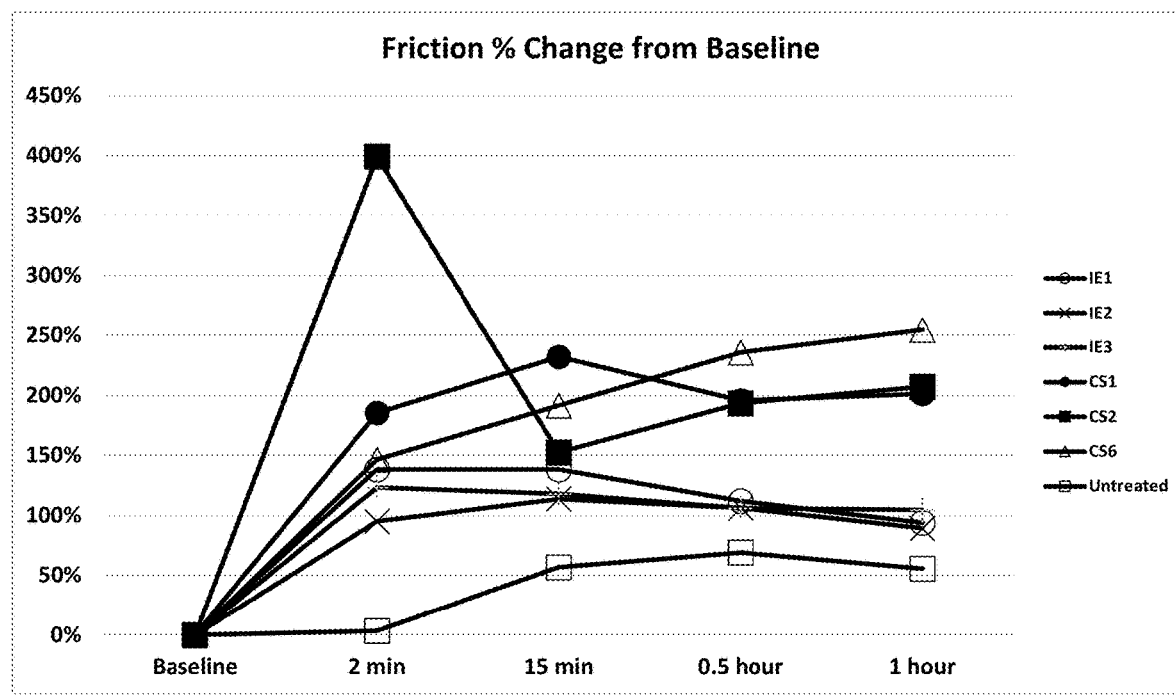
FIG. 2C depicts friction data of Inventive Examples vs. Comparative Samples.

Depicted in FIGS. 2B-2C is friction data for IE1-IE3 against three Comparative Samples and an untreated skin sample. Both overall friction change and average friction values are presented. In both cases, IE1-IE3 were all shown to produce lower friction against a surface of skin than all except the untreated test site. In other words, IE1-IE3 all produced lower friction than did all of the Comparative Samples.

Total Epidermal Water Loss

Figure 3A:
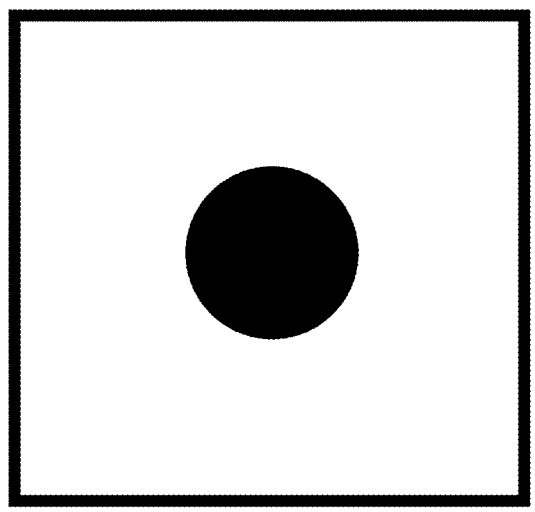
FIG. 3A illustrates a test site marked for obtaining TEWL data.

An AquaFlux™ Model AF200 (manufactured by Biox Systems Ltd.) was used for obtaining Trans Epidermal Water Loss (TEWL) data. Since TEWL data is affected by environmental humidity, the instrument was calibrated before each measurement. The instrument contains a probe to measure water as it escapes from within, and under, an epidermal layer of the skin. As indicated in FIG. 3A, a central area of each test site was measured at baseline (time=0), 30 minutes, 1 hour, and 2 hours.

Figure 3B:
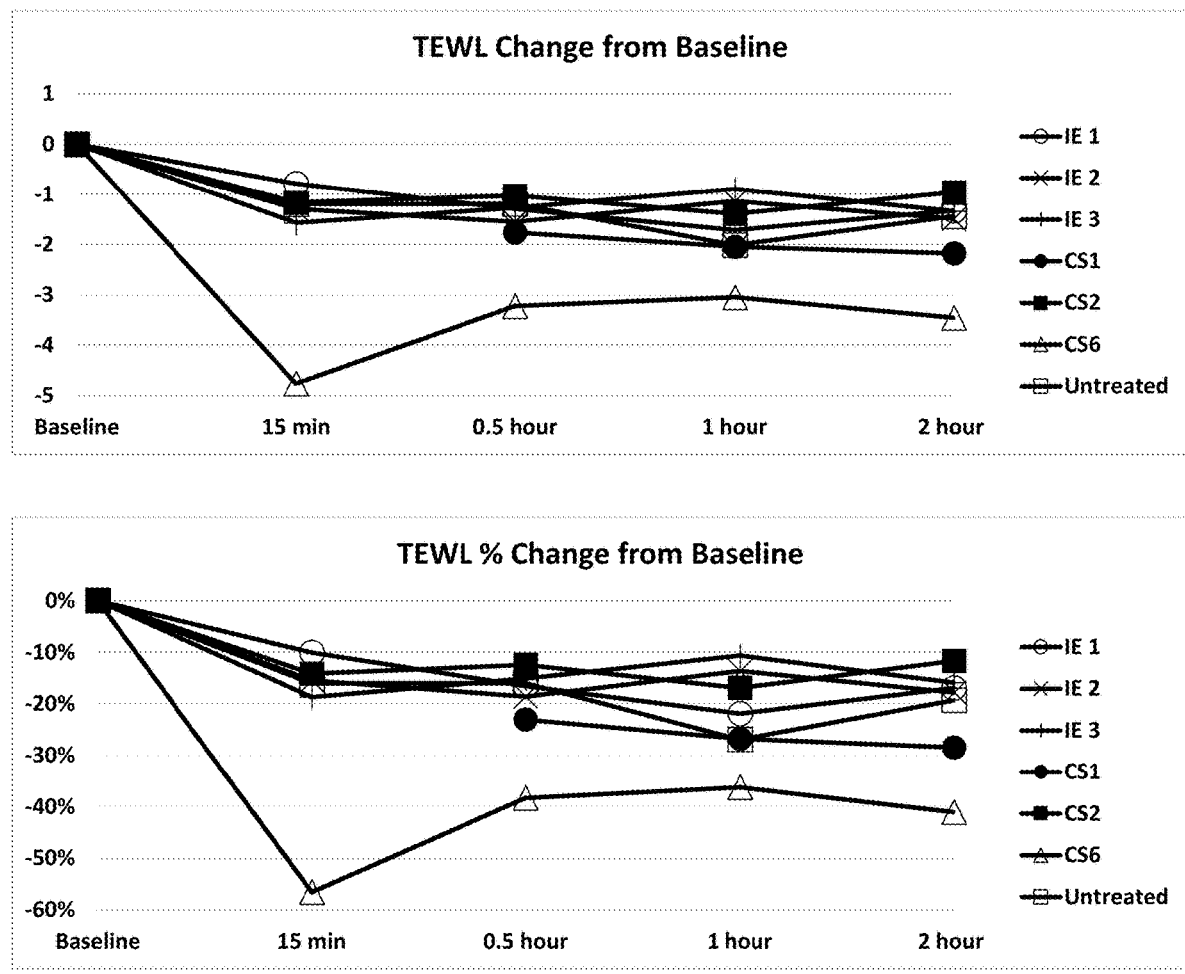
FIG. 3B illustrates TEWL data of Inventive Examples vs. Comparative Samples.

Depicted in FIG. 3B is TEWL data for IE1-IE3 against three Comparative Samples and an untreated skin sample. Both amount of water loss and percent water loss are presented. In both cases, IE1-IE3 were all shown to have comparable water loss (i.e., breathability) to both the untreated skin sample and Nivea® Breathable Nourishing Body Lotion. It should be noted that the latter was not part of the original testing, since Nivea® Breathable Nourishing Body Lotion was not yet commercialized when all other samples were tested. The same protocol was used, but results were only recorded at the most meaningful time points (hence Nivea® Breathable Nourishing Body Lotion not starting at time=0 in FIG. 3B).

Barrier Efficacy

Figure 4A:
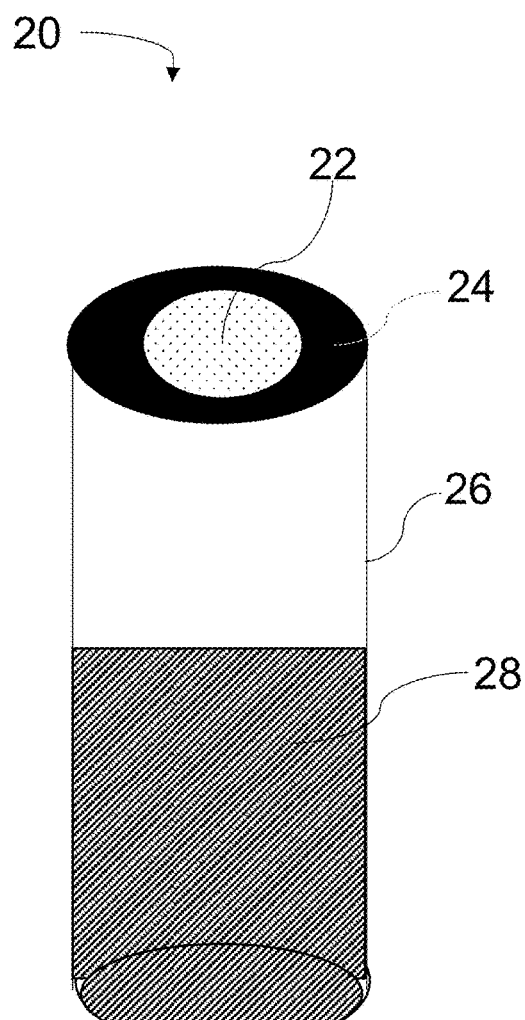
FIG. 4A illustrates a test apparatus for obtaining barrier efficacy data.
Figure 4B:
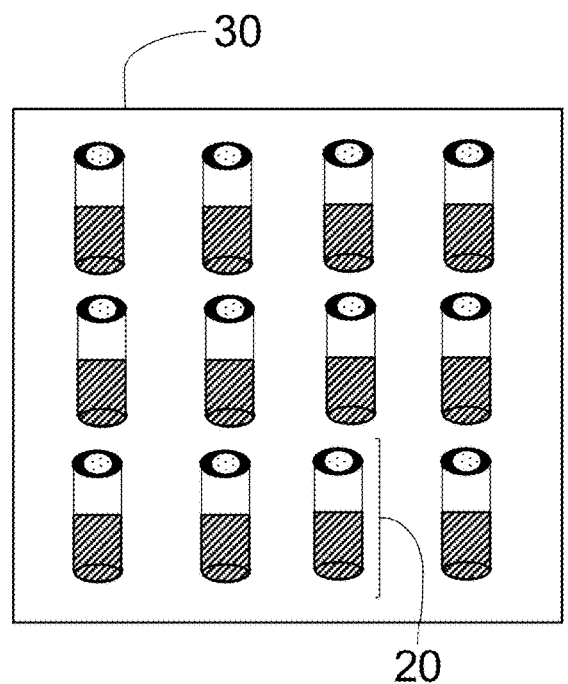
FIG. 4B illustrates a plurality of test apparatuses, such as that of FIG. 4A, in a box.

Barrier efficacy (i.e., breathability) data was obtained by preparing a test apparatus 20 (FIGS. 4A-4B) as follows: filter paper 22 (Whatman™ Filter Paper Cat. No. 1004-240 grade 4) was cut to obtain a circle with a diameter of 2 cm. An open-hole cap 24 of a vial 26 was unscrewed from the vial 26, and the filter paper 22 placed inside the open-hole cap 24. The vial 26 was filled with 10 g of deionized water 28. The open-hole cap 24, now with the filter paper 22 in place, was screwed back on to the vial 26 to form the test apparatus 20. An initial mass of the test apparatus 20 was obtained using an electronic balance (not shown).

For untreated filter paper 22, the test apparatus 20 was then placed into a box 30 with a plurality of holes (not shown), each for holding a test apparatus 20, and then into a walk-in chamber (not shown, custom-manufactured by Bally™) at 25° C. and a target average humidity of 40% for 24 hours, with start time and date noted.

Figure 4C:
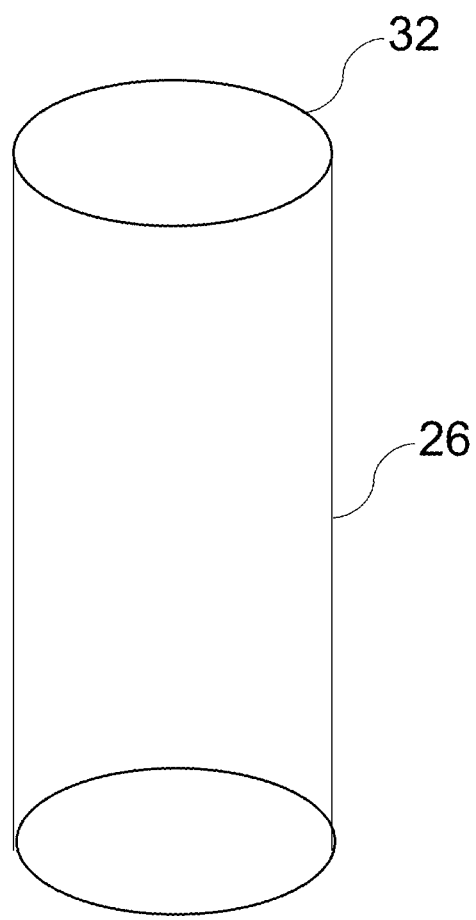
FIG. 4C illustrates a mouth of a vial of the test apparatus of FIG. 4A.

For filter paper 22 treated with a formulation, after obtaining the initial mass of the test apparatus 20, the open-hole cap 24 was then unscrewed from the vial 26 and the filter paper 22 moved from inside the open-hole cap 24 to a mouth 32 (FIG. 4C) of the vial 26. Tweezers (not shown) were used to handle the filter paper 22. For each formulation tested, an average of 0.05 g (i.e., 0.0475 g to 0.0525 g) of a formulation was scooped with a flat spatula (not shown) into a weigh boat (not shown) and measured on the electronic balance. To apply the formulation to the filter paper 22, the filter paper 22 was held with tweezers, and the formulation scooped with the flat spatula onto a surface of one side of the filter paper 22, forming a thin uniform film covering the entire surface. The treated filter paper 22 was measured to confirm that the entire mass of the formulation had been applied. Next, the filter paper 22 was placed back into the open-hole cap 24, with the treated side facing upward. The open-hole cap 24 was then screwed back on to the vial 26. An initial mass of the test apparatus 20 was then obtained using the electronic balance. The test apparatus 20 was then placed into the box 30 and into the chamber at 25° C. and a target average humidity of 40% for 24 hours, with start time and date noted.

For all samples, both untreated and treated, at 24 hours, the test apparatus 20 was removed from the chamber and mass obtained. Then the test apparatus 20 was placed back in the chamber. At 48 hours, the test apparatus 20 was again removed from the chamber and mass obtained.

The mass of the test apparatus 20 at 24 hours and 48 hours, respectively, was subtracted from the initial mass to obtain a difference in mass. Barrier efficacy (percent loss of water from vial) was calculated as:

Barrier Efficacy (%)=100−[(difference in mass of test apparatus/difference in mass of water)×100]

It should be noted that the measurement taken at 24 hours included loss of water from the formulation itself, and did not indicate loss of water due to barrier function. Untreated and treated samples were prepared and tested in triplicate, using the above protocol.

Figure 4D:
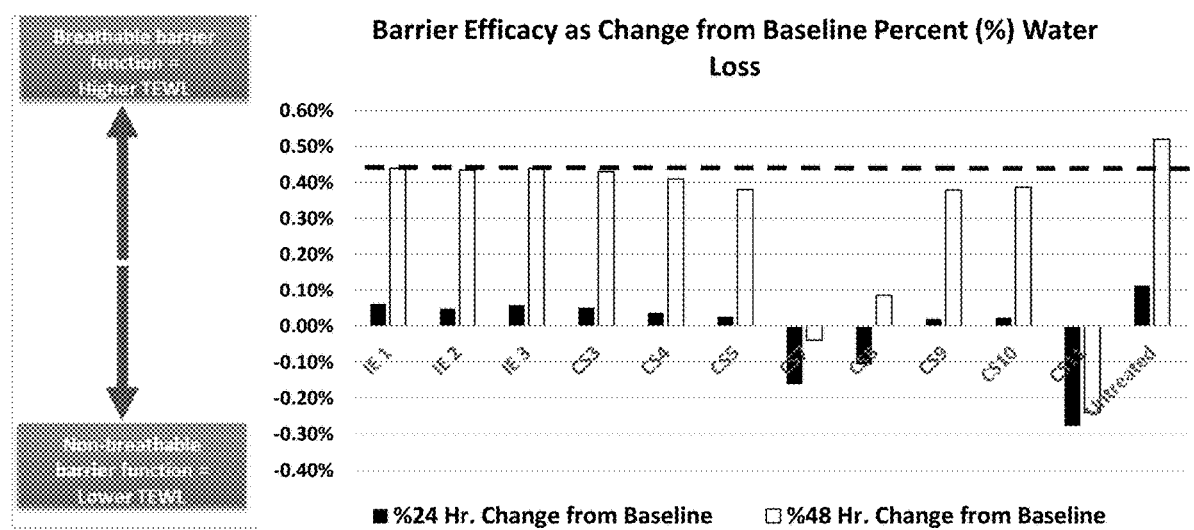
FIG. 4D depicts barrier efficacy data of Inventive Examples vs. Comparative Samples.

Depicted in FIG. 4D is barrier efficacy data for IE1-IE3 against several Comparative Samples and an untreated skin sample. Data is shown as a percent loss of water from the vial at both 24 hours and 48 hours. In order from left to right, the formulations indicated in FIG. 4D are IE1-IE3, CS3-CS5, CS7-CS11, and the untreated skin sample. IE1-IE3 were all shown to have superior or comparable barrier efficacy to all Neutrogena® samples, all Jergens® samples, Nivea® Breathable Nourishing Body Lotion, Eucerin® Original Healing, and Vaseline® Petroleum Jelly. Barrier efficacy for IE1-IE3 was acceptable compared that of the untreated skin sample.

Conductance

Figure 5A:
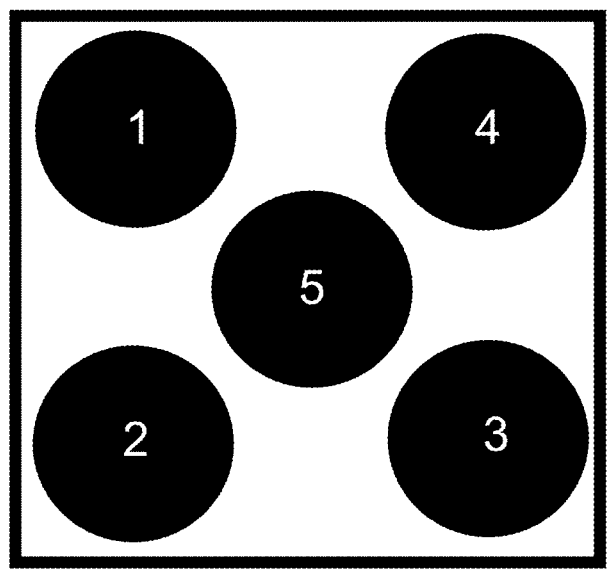
FIG. 5A illustrates a test site divided into five sub-sites for obtaining conductance data.

A DermaLab Combo Unit (manufactured by Cortex Technology) was used for obtaining conductance data. Such data is for determining external hydration of a surface of skin. As indicated in FIG. 5A, five sub-sites within each test site were marked. Measurements were obtained via a probe having a plurality of needles to contact the skin. Each sub-site was measured at baseline (time=0), 30 minutes, 1 hour, and 2 hours. For each time point, the five obtained values were averaged.

Figure 5B:
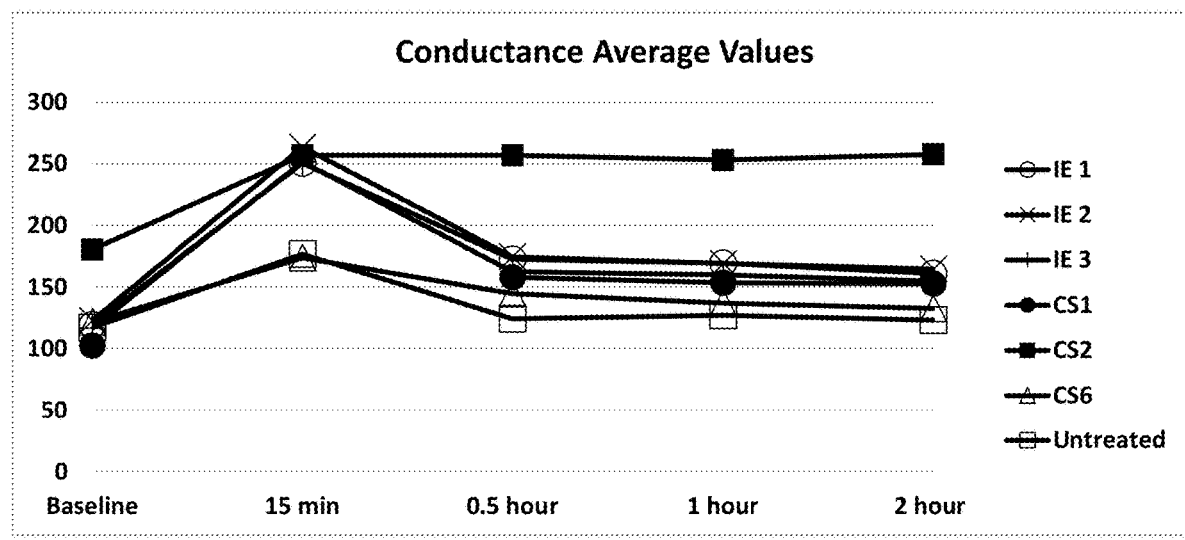
FIG. 5B depicts conductance data of Inventive Examples vs. Comparative Samples.
Figure 5C:
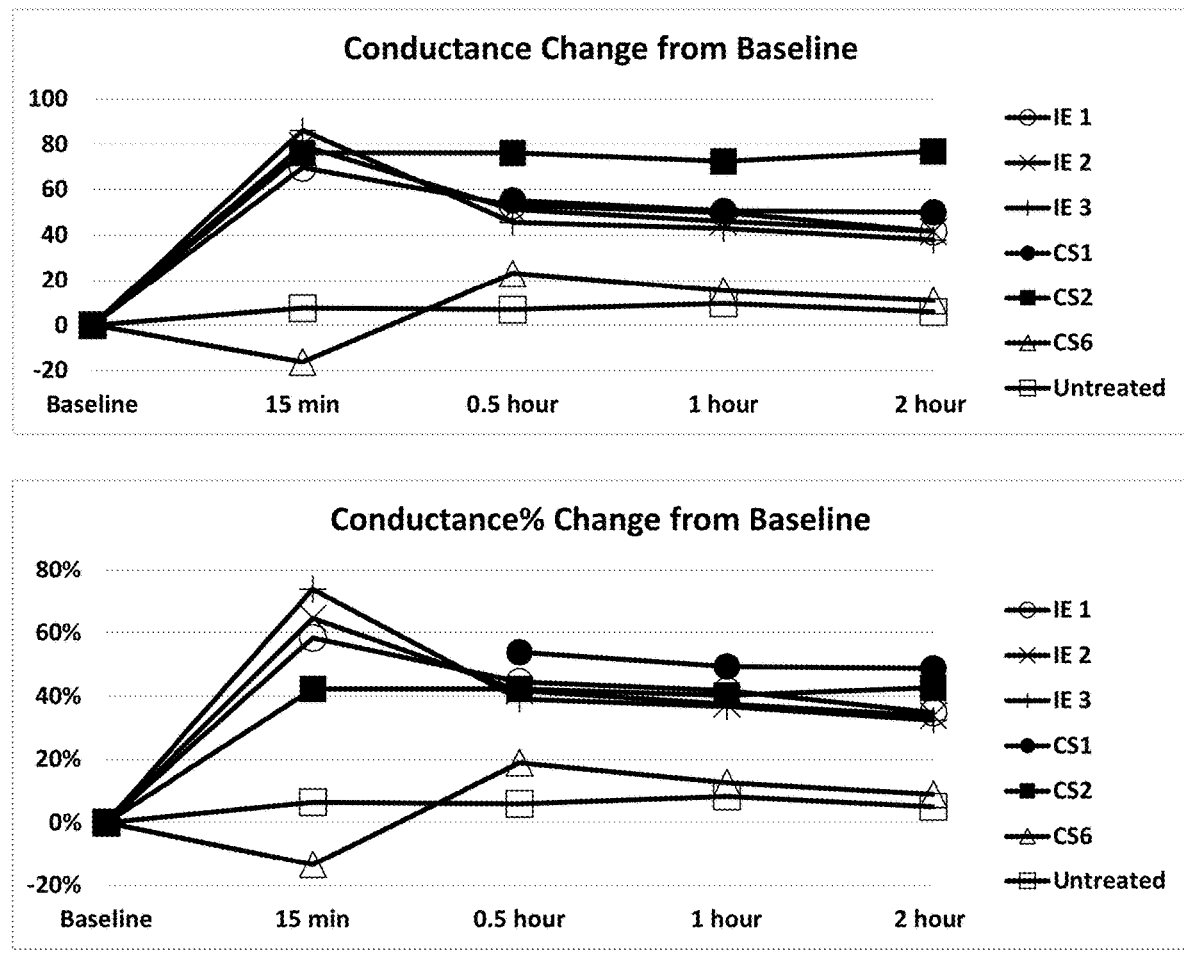
FIG. 5C depicts conductance data of Inventive Examples vs. Comparative Samples.

Depicted in FIGS. 5B-5C is conductance data for IE1-IE3 against three Comparative Samples and an untreated skin sample. Average conductance values, amount of change in conductance, and percent of change in conductance are all presented. In all cases, IE1-IE3 were all shown to have conductance that was: (i) better than that of both the untreated skin sample and petrolatum, (ii) comparable to that of Nivea® Breathable Nourishing Body Lotion, and (iii) acceptable compared to Jergens® Ultra Healing.

Conclusions

Based on the above-described data, IE1-IE3 all show a high-quality performance when compared to current commercial products. All Inventive Examples contain the combination of the at least one antimicrobial agent (in particular, the blend of phenoxyethanol, caprylhydroxamic acid, methylpropanediol, and water), sodium gluconate, ethylhexyl isononanoate, and the hyaluronic complex. While each of these components was added for its respective known function as described above, it was neither known nor expected that the presence of such a combination would possibly allow for properties such as those demonstrated by the data. This is particularly true for the at least one antimicrobial agent and sodium gluconate, whose functions are to disrupt microbial cells. None of the Comparative Samples have such a combination in their respective formulations. No combination of Comparative Samples and references stated in the Background section teaches, suggests, or discloses such a combination. Thus, it is believed that such a combination (found only within the Inventive Examples), with respective amounts of each component, is a unique combination that may contribute to the results demonstrated, i.e., formulations that perform comparably in the various demonstrated aspects against current commercial products lacking such a combination.

Furthermore, the Inventive Examples exhibit such properties while excluding (i.e., containing 0% of) ingredients that are considered undesirable by consumers. Non-limiting examples of such ingredients include parabens and BHT. Other ingredients, such as petrolatum, that typically create a heavy/greasy feeling during use, are also excluded from the Inventive Examples. The Inventive Examples also contain no dyes. This observation provides further reason to believe that the above-described combination of components may allow for the results observed.

What is claimed is:

1. A composition, for use as a body lotion for application to, and providing increased breathability and lower friction to, a surface of skin of a user, consisting of:
   a solvent;
   at least one humectant comprising glycerin;
   at least one thickener selected from the group consisting of a blend of acrylates and C10-30 alkyl acrylate cross-polymer, a blend of water, polyacrylamide, C13-14 isoparaffin, and laureth-7, and combinations thereof;
   at least one emollient comprising cetyl esters wax;
   at least one non-ionic primary emulsifier selected from the group consisting of ceteareth-20, a blend of glyceryl stearate and PEG-100 stearate, and combinations thereof;
   stearic acid;
   at least one silicone comprising dimethicone, phenyl trimethicone, and combinations thereof;
   aluminum starch octenylsuccinate;
   a plurality of antioxidants comprising a blend of water, pentylene glycol, lecithin, alcohol, ascorbyl palmitate, and tocopherol;
   sodium hydroxide;
   fragrance;
   from 0.1% to 1% of at least one antimicrobial agent by weight of said composition, comprising a blend of phenoxyethanol, caprylhydroxamic acid, methylpropanediol, and water;
   from 0.025% to 0.2% of sodium gluconate by weight of said composition;
   from 0.5% to 8% of ethylhexyl isononanoate by weight of said composition;
   from 0.005% to 0.04% of a hyaluronic complex by weight of said composition;

wherein said hyaluronic complex comprises a combination of sodium hyaluronate, hyaluronic acid, phenoxyethanol, and water;
wherein a ratio of sodium hyaluronate to hyaluronic acid is 1:1;
wherein a ratio of ethylhexyl isononanoate to said hyaluronic complex ranges from 12.5:1 to 1600:1; and
the composition excludes parabens, butylated hydroxytoluene, petrolatum, and dyes.

2. A composition, for use as a body cream for application to, and providing increased breathability and lower friction to, a surface of skin of a user, consisting of:
water;
at least one humectant comprising glycerin;
at least one thickener selected from the group consisting of xanthan gum and sodium acrylates crosspolymer-2 and combinations thereof;
at least one emollient selected from the group consisting of cetyl esters wax, shea butter, a blend of caprylic triglyceride and capric triglyceride, and combinations thereof;
at least one non-ionic primary emulsifier comprising ceteareth-20;
stearic acid;
at least one silicone
comprising dimethicone, phenyl trimethicone, a blend of dimethicone and dimethiconol, and combinations thereof;
aluminum starch octenylsuccinate;
a plurality of antioxidants
comprising a blend of water, pentylene glycol, lecithin, alcohol, ascorbyl palmitate, and tocopherol;
fragrance;
from 0.1% to 1% of a plurality of antimicrobial agents by weight of said composition;
wherein said plurality of antimicrobial agents comprises a blend of phenoxyethanol, caprylhydroxamic acid, methylpropanediol, and water;
from 0.025% to 0.2% of sodium gluconate by weight of said composition;
from 0.5% to 8% of ethylhexyl isononanoate by weight of said composition; and
from 0.005% to 0.04% of a hyaluronic complex by weight of said composition;
wherein said hyaluronic complex comprises a combination of sodium hyaluronate, hyaluronic acid, phenoxyethanol, and water;
wherein a ratio of sodium hyaluronate to hyaluronic acid is 1:1;
wherein a ratio of ethylhexyl isononanoate to said hyaluronic complex ranges from 12.5:1 to 1600:1; and
the composition excludes parabens, butylated hydroxytoluene, petrolatum, and dyes.

3. The composition of claim 2, wherein phenoxyethanol is 2-phenoxyethanol.

4. The composition of claim 1, wherein said solvent is water.

5. The composition of claim 1, wherein said ratio of ethylhexyl isononanoate to said hyaluronic complex is 200:1.

6. The composition of claim 1, wherein a ratio of sodium gluconate to ethylhexyl isononanoate ranges from 0.003:1 to 0.4:1.

7. The composition of claim 2, wherein said ratio of ethylhexyl isononanoate to said hyaluronic complex is 200:1.

8. The composition of claim 2, wherein a ratio of sodium gluconate to ethylhexyl isononanoate ranges from 0.003:1 to 0.4:1.

9. A composition, for use as a body cream for application to, and providing increased breathability and lower friction to, a surface of skin of a user, consisting of:
a solvent;
at least one humectant comprising glycerin, butylene glycol, and a blend of water, xylitylglucoside, anhydroxylitol, and xylitol, and combinations thereof;
at least one thickener comprising a blend of water, sodium acrylate, sodium acryloyldimethyl taurate copolymer, C15-19 alkane, polyglyceryl-6 laurate, and polyglycerin-6;
at least one emollient comprising dicaprylyl ether, isopropyl palmitate, glyceryl dilaurate, a blend of caprylic triglyceride and capric triglyceride, and combinations thereof;
at least one non-ionic primary emulsifier comprising glyceryl stearate, a blend of glyceryl stearate and PEG-100 stearate, and combinations thereof;
at least one silicone comprising dimethicone;
a plurality of antioxidants comprising a blend of water, pentylene glycol, lecithin, alcohol, ascorbyl palmitate, and tocopherol;
aluminum starch octenylsuccinate;
cetearyl alcohol;
stearic acid;
panthenol;
fragrance;
from 0.1% to 1% of at least one antimicrobial agent by weight of said composition, comprising a blend of phenoxyethanol, caprylhydroxamic acid, methylpropanediol, and water;
from 0.025% to 0.2% of sodium gluconate by weight of said composition;
from 0.5% to 8% of ethylhexyl isononanoate by weight of said composition;
from 0.005% to 0.04% of a hyaluronic complex by weight of said composition;
wherein said hyaluronic complex comprises a combination of sodium hyaluronate, hyaluronic acid, phenoxyethanol, and water;
wherein a ratio of sodium hyaluronate to hyaluronic acid is 1:1;
wherein a ratio of ethylhexyl isononanoate to said hyaluronic complex ranges from 12.5:1 to 1600:1; and
the composition excludes parabens, butylated hydroxytoluene, petrolatum, and dyes.

10. The composition of claim 9, wherein said solvent is water.

11. The composition of claim 9, wherein panthenol is D-panthenol.

12. The composition of claim 9, wherein said ratio of ethylhexyl isononanoate to said hyaluronic complex is 100:1.

13. The composition of claim 9, wherein a ratio of sodium gluconate to ethylhexyl isononanoate ranges from 0.003:1 to 0.4:1.

* * * * *